(12) United States Patent
Chang et al.

(10) Patent No.: US 6,638,762 B1
(45) Date of Patent: *Oct. 28, 2003

(54) TISSUE-VECTORS SPECIFIC REPLICATION AND GENE EXPRESSION

(75) Inventors: Yung-Nien Chang, Cockeysville, MD (US); Paul L. Hallenbeck, Gaithersburg, MD (US); Carl M. Hay, Damascus, MD (US); David A. Stewart, Eldersburg, MD (US)

(73) Assignee: Genetic Therapy, Inc., Gaithersburg, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 08/974,391

(22) Filed: Nov. 19, 1997

Related U.S. Application Data

(63) Continuation-in-part of application No. 08/487,992, filed on Jun. 7, 1995, now abandoned, which is a continuation-in-part of application No. 08/348,258, filed on Nov. 28, 1994, now abandoned, and a continuation-in-part of application No. 08/849,117, filed as application No. PCT/US95/15455 on Nov. 28, 1995, now Pat. No. 5,998,205, which is a continuation-in-part of application No. 08/487,992, filed on Jun. 7, 1995, now abandoned, which is a continuation-in-part of application No. 08/348,258, filed on Nov. 28, 1994, now abandoned.

(51) Int. Cl.⁷ .......................... C12N 15/00; C12N 15/63
(52) U.S. Cl. .................. 435/325; 435/69.1; 435/91.4; 435/320.1; 435/455; 514/44; 424/93.2
(58) Field of Search .................. 435/69.1, 320.1, 435/325, 455; 514/44; 424/93.2; 536/23.1

(56) References Cited

U.S. PATENT DOCUMENTS

| | | | |
|---|---|---|---|
| 5,112,767 A | 5/1992 | Roy-Burman et al. | 435/320.1 |
| 5,324,664 A | 6/1994 | Nunberg et al. | 435/320.1 |
| 5,358,866 A | 10/1994 | Mullen et al. | 435/240.2 |
| 5,416,017 A | 5/1995 | Burton et al. | 435/240.2 |
| 5,436,146 A | 7/1995 | Shenk et al. | 435/172.3 |
| 5,529,774 A | 6/1996 | Barba et al. | 424/93.21 |
| 5,585,096 A | 12/1996 | Martuza et al. | 424/93.2 |
| 5,591,439 A * | 1/1997 | Plotkin et al. | 424/199.1 |
| 5,601,818 A | 2/1997 | Freeman et al. | 424/93.21 |
| 5,624,820 A * | 4/1997 | Cooper | 435/69.1 |
| 5,624,830 A | 4/1997 | Mullen et al. | 435/172.3 |
| 5,631,236 A * | 5/1997 | Woo et al. | 514/44 |
| 5,677,178 A | 10/1997 | McCormick | 435/325 |
| 5,691,177 A | 11/1997 | Guber et al. | 435/172.3 |
| 5,698,443 A | 12/1997 | Henderson et al. | 435/320.1 |
| 5,728,379 A | 3/1998 | Martuza et al. | 424/93.2 |
| 5,747,469 A | 5/1998 | Roth et al. | 514/44 |
| 5,801,029 A | 9/1998 | McCormick | 435/172.3 |
| 5,804,407 A | 9/1998 | Tamaoki et al. | 435/69.1 |
| 5,830,686 A | 11/1998 | Henderson | 435/69.1 |
| 5,846,945 A | 12/1998 | McCormick | 435/44 |
| 5,856,181 A | 1/1999 | McCormick | 435/325 |
| 5,871,726 A | 2/1999 | Henderson et al. | 424/93.2 |
| 5,919,652 A * | 7/1999 | Pang et al. | 435/69.1 |
| 5,998,205 A | 12/1999 | Hallenbeck et al. | 435/325 |
| 6,051,417 A | 4/2000 | Henderson et al. | 435/252.3 |
| 6,057,299 A | 5/2000 | Henderson | 514/4 |
| 6,080,578 A | 6/2000 | Bischoff et al. | 435/325 |
| 6,133,243 A | 10/2000 | Kirn | 514/44 |
| 6,136,792 A | 10/2000 | Henderson | 514/44 |
| 6,197,293 B1 | 3/2001 | Henderson et al. | 424/93.2 |
| 6,254,862 B1 | 7/2001 | Little et al. | 424/93.2 |
| 6,296,845 B1 | 10/2001 | Sampson-Johannes et al. | 424/93.2 |
| 6,432,700 B1 | 8/2002 | Henderson et al. | 435/320.1 |
| 2001/0053768 A1 * | 12/2001 | Gregory et al. | |

FOREIGN PATENT DOCUMENTS

| | | |
|---|---|---|
| EP | 0 415 731 | 3/1991 |
| EP | 0 476 953 | 3/1992 |
| EP | 0 514 603 | 11/1992 |
| WO | WO 90/05180 | 5/1990 |
| WO | WO 92/03563 | 3/1992 |
| WO | WO 93/09239 | 5/1993 |
| WO | WO 93/10218 | 5/1993 |
| WO | WO 94/13824 | 6/1994 |
| WO | WO 94/18992 | 9/1994 |
| WO | WO 95/05835 | 3/1995 |
| WO | WO 95/11984 | 5/1995 |
| WO | WO 95/12660 | 5/1995 |

(List continued on next page.)

OTHER PUBLICATIONS

Abe, et al., "Characetization of cis–acting elements regulating transcription of the human DF3 breast carcinoma–associated antigen (MUC1) gene;" *Proc. Natl. Acad. Sci. USA*, 90:282–286 (Jan. 1993).

Grooteclaes, et al., "The 6–kilobase c–erbB2 promoter contains positive and negative regulatory elements functional in huyman mammary cell lines;" *Cancer Res.*, 54:4193–4199 (Aug. 1994).

Kovarik, et al., "Analysis of the tissue–specific promoter of the MUC1 gene;" *J. Biol. Chem.*, 268:9917–9926 (May 1993).

(List continued on next page.)

*Primary Examiner*—Dave T. Nguyen
(74) *Attorney, Agent, or Firm*—J. Timothy Meigs; Douglas A. Golightly; Thomas R. Savitsky

(57) ABSTRACT

The invention generally relates to cell-specific expression vectors. It particularly relates to targeted gene therapy using recombinant expression vectors and particularly adenovirus vectors. The invention specifically relates to replication-conditional expression vectors and methods for using them. Such vectors are able to selectively replicate in a target cell or tissue to provide a therapeutic benefit in a tissue from the presence of the vector per se or from one or more heterologous gene products expressed from the vector and distributed throughout the tissue. In such vectors, a gene essential for replication is placed under the control of a heterologous tissue-specific transcriptional regulatory sequence. Thus, replication is conditioned on the presence of a factor(s) that induces transcription or the absence of a factor(s) that inhibits transcription of the gene by means of the transcriptional regulatory sequence with this vector; therefore, a target tissue can be selectively treated.

59 Claims, 19 Drawing Sheets

FOREIGN PATENT DOCUMENTS

| WO | WO 95/14102 | 5/1995 |
|---|---|---|
| WO | WO 95/25807 | 9/1995 |
| WO | WO 96/01642 | 1/1996 |
| WO | WO 94/14875 | 5/1996 |
| WO | WO 96/17053 | 6/1996 |
| WO | WO 96/18418 | 6/1996 |
| WO | WO 96/33282 | 10/1996 |
| WO | WO 96/34969 | 11/1996 |
| WO | WO 96/36365 | 11/1996 |
| WO | WO 97/01358 | 1/1997 |
| WO | WO 97/29201 | 8/1997 |
| WO | WO 98/35028 | 8/1998 |
| WO | WO 98/39465 | 9/1998 |
| WO | WO 98/39466 | 9/1998 |
| WO | WO 98/39467 | 9/1998 |

OTHER PUBLICATIONS

Max–Audit, et al., "Transcriptional regulation of the pyruvate kinase erythroid–specific promoter;" *J. Biol. Chem.*, 268:5431–5437 (Mar. 1993).

Miller, et al., "Progress in transcriptionally targeted and regulatable vectors for genetic therapy," *Human Gene Therapy*, 8:803–815 (May 1, 1997).

Morishita, et al., "A novel promoter for vascular endothelial growth factor receptor (flt–1) that confers endothelial–specific gene expression;" *J. Biol. Chem.*, 270:27948–27953 (Nov. 1995).

Nakabayashi, et al., "A position–dependent silencer plays a major role in repressing α–fetoprotein expression in human hepatoma;" *Mol. Cll. Biol.*, 11:5885–5893 (Dec. 1991).

Richards, et al. "Transcriptional regulatory sequences of carcinoembryonic antigen: Identification and use with cytosine deaminase for tumor–specific gene therapy;" *Human Gene Therapy*, 6:881–893 (Jul. 1995).

Pang, et al., "Prostate Tissue specificity of the prostate–specific antigen promoter isolated from a patient with prostate cancer;" *Human Gene Therapy*, 6:1417–1426 (Nov. 1995).

Boviatsis, E.J., et al., "Antitumor activity and reporter gene transfer into rat brain neoplasms inoculated with herpes simplex virus vectors defective in thymidine kinase or ribonucleotide reductase," *Gene Therapy* 1:323–331 (Sep. 1994).

Chambers, R., et al., "Comparison of genetically engineered herpes simplex viruses for the treatment of brain tumors in a scid mouse model of human malignant glioma," *Proc. Natl. Acad. Sci. USA* 92:1411–1415 (Feb. 1995).

de Foresta, F., et al., "La transformation par le virus SV40 sensibilise les fibroblastes de peau human à l'action lytique du Parvovirus H–$_p$," *C. R. Soc. Biol.* 179:276–282 (1985).

Eiselein, J.E., et al., "Treatment of Transplanted Murine Tumors with an Oncolytic Virus and Cyclophosphamide," *Canc. Res. 38*:3817–3822 (1978).

Fresen, K.O., and Dübendorfer, A., "Elektrokinetisches Verhalten von Ehrlich–Aszites–Tumorzellen nach Infektion mit onkolytischem Influenzavirus," *Path. Microbiol. (Basel)* 40:227–228 (1974).

Fresen, K.O., and Dübendorfer, A., "Physicochemical Membrane Changes in Ehrlich Ascites Tumor Cells Infected with Oncolytic Influenza Virus," *Arch. Gesamte Virusforsch.* 41:267–276 (1973).

Fresen, K.O., "Physikochemische Veränderungen der Zelloberfläche von Ehrlich Aszites–Tumorenzellen nach Infektion mit onkolytischem Influenza–Virus," *Zentralbl. Bakt. Hyg., I.Abt. Orig. A 227*:409–413 (1974).

Furukawa, K., et al., Effect of virus–modified tumor cell extracts, autologous mononuclear cell infusions and interleukin–2 on oncolytic activity of effector cells of patients with advanced ovarian cancer, *Cancer Immunol. Immunother. 30*:126–132 (1989).

Hodes, M.E., et al., "Tissue Culture and Animal Studies with an Oncolytic Bovine Enterovirus (Bovine Entrovirus 1)," *Cancer Res. 33*:2408–2414 (1973).

Jacotot, H., "Pouvoir oncolytique in vivo du virus de Newcastle àl'é gard du sarcome ascitique de Yoshida," *C.R. Hebd. Seances Acad. Sci. Paris, Ser. D 264*:2602–2603 (1967).

Lorence, R.M., et al., "Newcastle Disease Virus as an Antineoplastic Agent: Induction of Tumor Necrosis Factor–α and Augmentation of Its Cytotoxicity," *J. Natl. Cancer Inst. 80*:1305–1312 (1988).

Neagoe, G., and Stoian, M., "Methods of Active Immunotherapy and Viral Oncolysis in some Forms of Cancer," *Rev. Roum. Méd.—Méd. Int. 24*:125–142 (1986).

Schlechte, H., et al., "Wirtsbereichstestung von tumorselektiven Clostridium–butyricum–Stämmen mit den Phagen 5," *Arch. Geshwulstforsch. 50*:53–57 (1980).

Shoham, J., et al., "Augmentation of Tumor Cell Immunogenicity by Viruses—An Approach to Specific Immunotherapy of Cancer," *Nat. Immun. Cell Growth Regul. 9*:165–172 (1990).

Sinkovics, J.G., "Programmed Cell Death (Apoptosis): Its Virological and Immunological Connections (A Review)," *Acta Microbiol. Hung. 38*:321–334 (1991).

Sinkovics, J.G., "Oncogenes–Antioncogenes and Virus Therapy of Cancer," *Anticancer Res. 9*:1281–1290 (1989).

Tsypkin, L.B., et al., "The Morphology of Tumors of the Human Gastrointestinal Tract in Short–Term Organ Culture and the Reaction of these Tumors to Infection with Poliovirus," *Cancer 38*:1796–1806 (1976).

Yohn, D.S., et al., "Oncolytic Potentials of Nonhuman Viruses for Human Cancer. II. Effects of Five Viruses on Heterotransplantabale Human Tumors," *J. Natl. Canc. Inst. 41*:523–529 (1968).

Mettler, N.E., et al., "Virus Inoculationin Mice Bearing Ehrlich Ascitic Tumors: Antigen Production and Tumor Regression," *Infect. Immun. 37*:23–37 (1982).

Berkner, K. L., "Development of Adenovirus Vectors for the Expression of Heterologous Genes," *Biotechniques* 6:616–629, Eaton Publishing, London, UK (1988).

Friedman, J.M. and Babiss, L.E., "Adenoviral Vectors and Liver Specific Gene Control," in: *Transcriptional Control Mechanisms*, New York: Alan R. Liss, Inc., pp. 421–435 (1987).

Hallenbeck, P.L., et al., "A Novel Tumor–Specific Replication–Restricted Adenoviral Vector for Gene Therapy of Hepatocellular Carcinoma," *Human Gene Therapy* 10:1721–1733 (1999).

Kenney, S., and Pagano, J.S., "Viruses as Oncolytic Agents: a New Age for 'Therapeutic' Viruses ?," *J. Natl. Cancer Inst. 86*:1185–1186 (Aug. 1994).

Sinkovics, J.G., "Viral Oncolysates as Human Tumor Vaccines," *Intern. Rev. Immunol. 7*:259–287 (1991).

Taneja, S.S., et al., "In vitro target specific gene therapy for prostate cancer utilizing a prostate specific antigen promoter–driven adenoviral vector," *Proc. Am. Assn. Canc. Res. 35*:375, abstract No. 2236, American Association for Cancer Research, Washington, DC (Mar. 1994).

Zieliński, T., and Jordan, E., "Late Results of Clinical Observation of the Oncolytic Action of Adenoviruses in Cervix Uteri Carcinoma," *Nowotwory (Poland) 19*(3): 217–221 (1969).

Hallenbeck, P.L. et al., "Novel tumor specific replication competent adenoviral vectors for gene therapy of cancer," from the Fifth International Conference on Gene Therapy of Cancer, San Diego, CA, Nov. 14–16, 1996, *Cancer Gene Ther. 3*:s19 (Nov. 1996).

Hallenbeck, P.L. et al., "Novel tumor specific replication restricted adenoviral vector for gene therapy of liver cancer," from the Sixth International Conference on Gene Therapy of Cancer, San Diego, CA, Nov. 20–22, 1997, *Cancer Gene Ther. 4*:s22 (Nov. 1997).

Chellappan, S. et al., "Adenovirus E14, simian virus 40 tumor antigen, and human papillomavirus E7 protein share the capacity to disrupt the interaction between transcription factor E2F and the retinoblastoma gene product," *Proc. Natl. Acad. Sci. USA 89*:4549–4553 (1992).

Chen, S.–H. et al., "Gene therapy for brain tumors: Regression of experimental gliomas by adenovirus–mediated gene transfer in vivo," *Proc. Natl. acad. Sci. USA 91*:3054–3057 (Apr. 1994).

Coghlan, A., "Gene dream fades away," *New Scientist 145*:14–15 (Nov. 1995).

Cornelis, J. et al., "Transformation of Human Fibroblasts by Ionizing Radiation, a Chemical Carcinogen, or Simian Virus 40 Correlates with an Increase in Susceptibility to the Autonomous Parvoviruses H–1 Virus and Minute Virus of Mice," *J. Virol. 62*:1679–1686 (1988).

Crystal, R., "Transfer of Genes to Humans: Early Lessons and Obstacles to Success," *Science 270*:404–410 (Oct. 1995).

Culver, K. et al., "In Vivo Gene Transfer with Retroviral Vector–Producer Cells for Treatment of Experimental Brain Tumors," *Science 256*:1550–1552 (1992).

Dillon, N., "Regulating gene expression in gene therapy," *TIBTECH 11*:167–173 (May 1993).

Dooley, T. et al., "Transactivation of the adenovirus EIIa promoter in the absence of adenovirus E1A protein is restricted to mouse oocytes and preimplantation embryos," *Development 107*:945–956 (1989).

Dynan, W., "Modularity in Promoters and Enhancers," *Cell 58*:1–4 (1989).

Fattaey, A. et al., "Replication of Adenovirus Mutants in Human Cancer Cells," Abstracts of papers presented at the 1994 meeting on Molecular Biology of Papovaviruses and Adenoviruses, Aug. 17–Aug. 21, 1994, Cold Spring Harbor Laboratory, Cold Spring Harbor, New York.

Freytag, S. et al., "A Novel Three–Pronged Approach to Kill Cancer Cells Selectively: Concomitant Viral, Double Suicide Gene, and Radiotherapy," *Human Gene Therapy 9*:1323–1333 (Jun. 1998).

Friedman, J. et al., "Cellular Promoters Incorporated into the Adenovirus Genome: Cell Specificity of Albumin and Immunoglobulin Expression," *Mol. Cell. Biol. 6*:3791–3797 (1986).

Fujiwara, T. et al., "A Retroviral Wild–type p53 Expression Vector Penetrates Human Lung Cancer Spheroids and Inhibits Growth by Inducing Apoptosis," *Cancer Res. 53*:4129–4133 (Sep. 1993).

Gerard, R. and R. Meidell, "Adenovirus–Mediated Gene Transfer," *TCM 3*:171–177 (May 1993).

Gordon, E. and W. Anderson, "Gene therapy using retroviral vectors," *Curr. Op. Biotechnol. 5*:611–616 (Dec. 1994).

Graham, F., "Growth of 293 Cells in Suspension Culture," *J. Gen. Virol. 68*:937–940 (1987).

Günzburg, W. and B. Salmons, "Mouse Mammary Tumor Virus Mediated Transfer and Expression of Neomycin Resistance to Infected Cultured Cells," *Virology 155*:236–248 (1986).

Günzburg, W. and B. Salmons, "Virus vector design in gene therapy," *Mol. Med. Today 1*:410–417 (Dec. 1995).

Haj–Ahmad, Y. and F. Graham, "Development of a Helper–Independent Human Adenovirus Vector and Its Use in the Transfer of the Herpes Simplex Virus Thymidine Kinase Gene," *J. Virol. 57*:267–274 (1986).

Harris, J. et al., "Gene therapy of cancer using tumour–specific prodrug activation," *Gene Therapy 1*:170–175 (May 1994).

Hitt, M. and F. Graham, "Adenovirus E1A under the Control of Heterologous Promoters: Wide Variation in E1A Expression Levels has Little Effect on Virus Replication," *Virology 179*:667–678 (1990).

Horvath, J. et al., "Complementation of Adenovirus Early Region 1a and 2a Mutants by Epstein–Barr Virus Immortalized Lymphoblastoid Cell lines," *Virology 184*:141–148 (1991).

Horwitz, M., "Adenoviral Diseases," in *Virology*, B.N. Fields, et al., eds., Raven Press, New York, pp. 477–495 (1985).

Huber, B. et al., "Retroviral–mediated gene therapy for the treatment of hepatocellular carcinoma: An innovative approach for cancer therapy," *Proc. Natl. Acad. Sci. USA 88*:8039–8043 (1991).

Imperiale, M. et al., "Common Control of the Heat Shock Gene and Early Adenovirus Genes: Evidence for a Cellular E1A–like Activity," *Mol. Cell. Biol. 4*:867–874 (1984).

Kaneko, S. et al., "Adenovirus–mediated Gene Therapy of Hepatocellular Carcinoma using Cancer–specific Gene Expression," *Cancer Res. 55*:5283–5287 (Nov. 1995).

Ko, S.–C. et al., "Osteocalcin Promoter–based Toxic Gene Therapy for the Treatment of Osteosarcoma in Experimental Models," *Cancer Res. 56*:4614–4619 (Oct. 1996).

La Thangue, N. and P. Rigby, "An Adenovirus E1A–like Transcription Factor is Regulated during the Differentiation of Murine Embryonal Carcinoma Stem Cells," *Cell 49*:507–513 (1987).

Ledley, F., "Nonviral Gene Therapy: The Promise of Genes as Pharmaceutical Products," *Human Gene Therapy 6*:1129–1144 (Sep. 1995).

Lewin, B., "Oncogenic Conversion by Regulatory Changes in Transcription Factors," *Cell 64*:303–312 (1991).

Manome, Y. et al., "Enhancer Sequences of the DF3 Gene Regulate Expression of the Herpes Simplex Virus Thymidine Kinase Gene and Confer Sensitivity of Human Breast Cancer Cells to Gancyclovir," *Cancer Res. 54*:5408–5413 (Oct. 1994).

Mastrangelo, M. et al., "Gene Therapy for Human Cancer: An Essay for Clinicians," *Seminars in Oncology 23*:4–21 (Feb. 1996).

Missero, C. et al., "Skin–specific Expression of a Truncated E1a Oncoprotein Binding to p105–Rb Leads to Abnormal Hair Follicle Maturation Without Increased Epidermal Proliferation," *J. Cell. Biol. 121*:1109–1120 (Jun. 1993).

Moran, E., "Interaction of adenoviral proteins with pRB and p53," *FASEB J. 7*:880–885 (Jul. 1993).

Mulligan, R., "The Basic Science of Gene Therapy," *Science* 260:926–931 (May 1993).

Nakamura, Y. et al., "Adoptive Immunotherapy with murine Tumor–specific T Lymphocytes Engineered to Secrete Interleukin 2," *Cancer Res.* 54:5757–5760 (Nov. 1994).

Ohno, T. et al., "Gene Therapy for Vascular Smooth Muscle Cell Proliferation After Arterial Injury," *Science* 265:781–784 (Aug. 1994).

Ookawa, K. et al., "Reconstitution of the RB gene suppresses the growth of small lung cell carcinoma cells carrying multiple genetic alterations," *Oncogene* 8:2175–2181 (Aug. 1993).

Orkin, S. and A. Motulsky, "Report and Recommendations of the Panel to Assess the NIH Investment in Research on Gene Therapy," Published by NIH at Bethesda, MD, Dec. 7, 1995.

Osaki, T. et al., "Gene Therapy for Carcinoembryonic Antigen–producing Human Lung Cancer Cells by Cell Type–specific Expression of Herpes Simplex Virus Thymidine Kinase Gene," *Cancer Res.* 54:5258–5261 (Oct. 1994).

Pennisi, E., "Will a Twist of Viral Fate Lead to a New Cancer Treatment?" *Science* 274:342–343 (Oct. 1996).

Pulsieux, A. et al., "p53 as a growth suppressor gene in HBV–related hepatocellular carcinoma cells," *Oncogene* 8:487–490 (Feb. 1993).

Ringold, G. et al., "Glucocorticoid–stimulated accumulation of mouse mammary tumor virus RNA: Increased rate of synthesis of viral RNA," *Proc. Natl. Acad. Sci. USA* 74:2879–2883 (1977).

Rodriquez, R. et al., "Prostate Attenuated Replication Competent Adenovirus (ARCA) CN706: A Selective Cytotoxic for Prostate–specific Antigen–positive Prostate Cancer Cells," *Cancer Res.* 57:2559–2563 (Jul. 1997).

Russell, S. et al., "Transformation–Dependent Expression of Interleukin Genes Delivered by a Recombinant Parvovirus," *J. Virol.* 66:2821–2828 (1992).

Russell, S., "Replicating Vectors for Gene Therapy of Cancer: Risks, Limitations and Prospects," *Eur. J. Cancer* 30A:1165–1171 (Aug. 1994).

Salmons, B. and W. Günzburg, "Targeting of Retroviral Vectors for Gene Therapy," *Human Gene Therapy* 4:129–141 (Apr. 1993).

Schrewe, H. et al., "Cloning of the Complete Gene for Carcinoembryonic Antigen: Analysis of Its Promoter Indicates a Region Conveying Cell Type–Specific Expression," *Mol. Cell. Biol.* 10:2738–2748 (1990).

Shenk, T. et al., "Functional Analysis of Adenovirus–5 Host–range Deletion Mutants Defective for Transformation of Rat Embryo Cells," *Cold Spring Harbor Symp. Quant. Biol.* 44:367–375 (1979).

Shimizu, E. et al., "RB protein status and clinical correlation from 171 cell lines representing lung cancer, extrapulmonary small cell carcinoma, and mesothelioma," *Oncogene* 9:2441–2448 (Sep. 1994).

Shingu, M. et al., "Therapeutic effects of bovine enterovirus infection on rabbits with experimentally induced adult T cell leukaemia," *J. Gen. Virol.* 72:2031–2034 (1991).

Sikora, K., "Genetic approaches to cancer therapy," *Gene Therapy* 1:149–151 (Jan. 1994).

Smith, M. et al., "Surfactant Protein A–Directed Toxin Gene Kills Lung Cancer Cells In Vitro," *Human Gene Therapy* 5:29–35 (Jan. 1994).

Spergel, J. and S. Chen–Kiang, "Interleukin 6 enhances a cellular activity that functionally substitutes for E1A protein in transactivation," *Proc. Natl. Acad. Sci. USA* 88:6472–6476 (1991).

Spergel, J. et al., "NF–II6, a Member of the C/EBP Family, Regulates E1A–Responsive Promoters in the Absence of E1A," *J. Virol.* 66:1021–1030 (1992).

Stratford–Perricaudet, L. and M. Perricaudet, "Gene transfer into animals: the promise of adenovirus," *Human Gene Transfer* 219:51–61 (1991).

Vile, R. and I. Hart, "Use of Tissue–specific Expression of the Herpes Simplex Virus Thymidine Kinase Gene to Inhibit Growth of Established Murine Melanomas following Direct Intratumoral injection of DNA," *Cancer Res.* 53:3860–3864 (Sep. 1993).

Vile, R. and I. Hart, "In Vitro and In Vivo Targeting of Gene Expression to Melanoma Cells," *Cancer Res.* 53:962–967 (Mar. 1993).

Vile, R., "Gene Therapy and Cytokines," *Brit. J. Canc.* 69(Suppl. 21):3, Abstract s7 (Mar. 1994).

Vile, R., "Direct Gene Transfer to Tumour Cells In Vivo," *Gene Therapy* 1(Supp. 2):s6, abstract A23 (Nov. 1994).

Vile, R. et al., "Strategies for achieving multiple layers of selectivity in gene therapy," *Molec. Med. Today* 4:84–92 (Feb. 1998).

Yamada, M. et al., "Overproduction of the protein product of a nonselected foreign gene carried by an adenovirus vector," *Proc. Natl. Acad. Sci. USA* 82:3567–3571 (1985).

Yang, Y. et al., "MHC Class I–Restricted Cytotoxic T Lymphocytes to Viral Antigens Destroy Hepatocytes in Mice Infected with E1–deleted Recombinant Adenoviruses," *Immunity* 1:433–442 (Aug. 1994).

* cited by examiner

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 1
ggccgcatgc atgtttaaac g                                          21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
gatccgttta aacatgcatg c                                          21

<210> SEQ ID NO 3
<211> LENGTH: 20

```
<212> TYPE: DNA
<213> ORGANISM: Artificial Sequence
<220> FEATURE:
<223> OTHER INFORMATION: Description of Artificial Sequence: primer

<400> SEQUENCE: 3
agcaagaagc cacggaagtc                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
aggtcgcaga tcgtcggtat                                                20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 5
gaccgtttac gtggagactc gc                                             22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 6
accgccaaca ttacagagtc g                                              21

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: primer

<400> SEQUENCE: 7
gggcgcgccc tggaaagtcc ggctggggcg gggactgtgg gtttcagggt agaactgcgt    60
gtggaa                                                               66

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 8
cgggacaggg agcggttaga agggtgggc tattccggga agtggtgggg ggagggaact     60
agta                                                                 64

<210> SEQ ID NO 9
<211> LENGTH: 63
<212> TYPE: DNA
<213> ORGANISM: Artificial Sequence
<220> FEATURE:
```

```
<223> OTHER INFORMATION: Description of Artificial Sequence: primer

<400> SEQUENCE: 9
gatctactag ttccctcccc ccaccacttc ccggaatagc cccacccttc taaccgctcc        60
ctg                                                                      63

<210> SEQ ID NO 10
<211> LENGTH: 71
<212> TYPE: DNA
<213> ORGANISM: Artificial Sequence
<220> FEATURE:
<223> OTHER INFORMATION: Description of Artificial Sequence: primer

<400> SEQUENCE: 10
tcccgttcca cacgcagttc taccctgaaa cccacagtcc ccgcccagc cggactttcc         60 agggcgcgcc c                                                             71

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 11
gacccgggcg cgccggagca gtgctattca aaccatccag                              40

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 12
cgagatctac tagttctgca ccaataggtt aatgagtgtc                              40

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 13
gacccgggcg cgcctctgtc accttcctgt tgg                                     33

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 14
cgagatctac tagttctctg ctgtctgctc tgtc                                    34
```

TISSUE-VECTORS SPECIFIC REPLICATION AND GENE EXPRESSION

CROSS REFERENCE TO RELATED APPLICATIONS

This application is a continuation-in-part claiming benefit under 35 USC §120 of U.S. application Ser. No. 08/487,992, filed Jun. 7, 1995 (abandoned), which is a continuation-in-part of U.S. application Ser. No. 08/348,258, filed Nov. 28, 1994 (abandoned). This application is also a continuation-in-part application of U.S. application Ser. No. 08/849,117 filed Aug. 1, 1997 (U.S. Pat. No. 5,998,205), which is a §371 of PCT/US95/15455, which has an international filing date under the PCT of Nov. 28, 1995, and which entered the United States national phase on May 28, 1997, which is a continuation-in-part application of U.S. application Ser. No. 08/487,992, filed Jun. 7, 1995 (abandoned), which is a continuation-in-part of U.S. application Ser. No. 08/348, 258, filed Nov. 28, 1994 (abandoned), all incorporated herein in their entirety by reference.

BACKGROUND OF THE INVENTION

1. Field of the Invention

The invention generally relates to cell-specific expression vectors. It particularly relates to targeted gene therapy using recombinant expression vectors and particularly adenovirus vectors. The invention specifically relates to modulatable replication-conditional expression vectors and methods for using them. Such vectors are able to selectively replicate in a target cell or tissue to provide a therapeutic benefit in a tissue from the presence of the vector per se or from one or more heterologous gene products expressed from the vector and distributed throughout the tissue, and which vectors are designed so that replication and gene expression from the vector can be modulated.

In such vectors, a gene essential for replication is placed under the control of a heterologous tissue-specific transcriptional regulatory sequence. Thus, replication is conditioned on the presence of a factor(s) that induces transcription or the absence of a factor(s) that inhibits transcription of the gene by means of the transcriptional regulatory sequence.

Preferred vectors contain a heterologous gene that produces a product that increases or inhibits viral replication. Such genes are useful for modulating viral replication and thus also for modulating expression of genes in the vector. With these vectors, therefore, the vector can be expressed in a desirable cell, target tissue can be selectively treated, and replication and expression modulated.

The invention also relates to cells and/or methods to produce multiple heterologous gene products in high quantity from essentially one promoter element.

The invention also relates to methods of using the vectors to screen a tissue for the presence or absence of transcriptional regulatory functions that permit vector replication by means of the transcriptional regulatory sequence.

2. Background Art

Targeting Vectors

The introduction of exogenous genes into cells in vitro or in vivo, systemically or in situ, has been of limited use for compositions in which it would be disadvantageous for non-target cells to take up the exogenous gene. One strategy to overcome this problem is to develop administration procedures or vectors that target a specific cell-type. Using systemic administration, attempts have been made to direct exogenous genes to myocytes and muscle cells by direct injection of DNA, to direct the exogenous DNA to hepatocytes using DNA-protein complexes, and to endothelial cells using liposomes.

Using in situ administration, retroviral replication functions have been utilized to target cells that are actively replicating.

Thus far, the ability to target cells has been limited, however, by the lack of cell-type specificity and low gene transfer efficiencies. The limited ability to target an exogenous gene to diseased cells in an organism, while avoiding (eliminating) uptake of the gene by normal, untargeted cells, particularly has been an obstacle to developing effective gene-transfer-based therapies for diseases in animals and humans.

One especially difficult challenge is targeting tumor cells. Many seemingly promising strategies for these cells, moreover, are limited to one or a few cell-types.

The present invention, in one aspect, provides a way to deliver an exogenous gene efficiently, with high distribution in a tumor and in a controlled manner.

Adenoviruses Generally

Adenoviruses are nonenveloped, regular icosohedrons. The protein coat (capsid) is composed of 252 capsomeres of which 240 are hexons and 12 are pentons. Most of the detailed structural studies of the adenovirus polypeptides have been done for adenovirus types 2 and 5. The viral DNA is $23.85 \times 10^6$ daltons for adenovirus 2 and varies slightly in size depending on serotype. The DNA has inverted terminal repeats and the length of these varies with the serotype.

The replicative cycle is divided into early (E) and late (L) phases. The late phase defines the onset of viral DNA replication. Adenovirus structural proteins are generally synthesized during the late phase. Following adenovirus infection, host DNA and protein synthesis is inhibited in cells infected with most serotypes. The adenovirus lytic cycle with adenovirus 2 and adenovirus 5 is very efficient and results in approximately 10,000 virions per infected cell along with the synthesis of excess viral protein and DNA that is not incorporated into the virion. Early adenovirus transcription is a complicated sequence of interrelated biochemical events, but it entails essentially the synthesis of viral RNAs prior to the onset of viral DNA replication.

The organization of the adenovirus genome is similar in all of the adenovirus groups and specific functions are generally positioned at identical locations for each serotype studied. Early cytoplasmic messenger RNAs are complementary to four defined, noncontiguous regions on the viral DNA. These regions are designated (E1–E4). The early transcripts have been classified into an array of immediate early (E1a), delayed early (E1b, E2a, E2b, E3 and E4), and intermediate (IVa2.IX) regions.

E1a is a transactivator of multiple gene products in adenovirus through activation of the E1b, E2, E3 and E4 promoters. The E1a region is involved in transcriptional transactivation of viral and cellular genes as well as transcriptional repression of other sequences. The E1a gene exerts an important control function on all of the other early adenovirus messenger RNAs. In normal tissues, in order to transcribe regions E1b, E2a, E2b, E3, or E4 efficiently, active E1a product is required.

The E1b region is required for the normal progression of viral events late in infection. The E1b product acts in the host nucleus. Mutants generated within the E1b sequences exhibit diminished late viral mRNA accumulation as well as impairment in the inhibition of host cellular transport normally observed late in adenovirus infection (Berkner, K. L., *Biotechniques* 6:616–629 (1988)). E1b is required for altering functions of the host cell such that processing and transport are shifted in favor of viral late gene products. These products then result in viral packaging and release of virions. E1b produces a 19 kD protein that prevents apoptosis. E1b also produces a 55 kD protein that binds to p53.

For a complete review on adenoviruses and their replication, see Horwitz, M. S., *Virology* 2d ed., Fields, B. N., eds., Raven Press Limited, New York (1990), Chapter 60, pp. 1679–1721.

Adenovirus as Recombinant Delivery Vehicle

Adenovirus provides advantages as a vector for adequate gene delivery for the following reasons. It is a double stranded DNA nonenveloped virus with tropism for the human respiratory system and gastrointestinal tract. It causes a mild flu-like disease. Adenoviral vectors enter cells by receptor mediated endocytosis. The large (36 kilobase) genome allows for the removal of genes essential for replication and nonessential regions so that foreign DNA may be inserted and expressed from the viral genome. Adenoviruses infect a wide variety of cell types in vivo and in vitro. Adenoviruses have been used as vectors for gene therapy and for expression of heterologous genes. The expression of viral or foreign genes from the adenovirus genome does not require a replicating cell. Adenovirus vectors rarely integrate into the host chromosome; the adenovirus genome remains as an extrachromosomal element in the cellular nucleus. There is no association of human malignancy with adenovirus infection; attenuated strains have been developed and have been used in humans for live vaccines.

For a more detailed discussion of the use of adenovirus vectors for gene therapy, see Berkner, K. L., *Biotechniques* 6:616–629 (1988); Trapnell, B. C., *Advanced Drug Delivery Reviews* 12:185–199 (1993).

Adenovirus vectors are generally deleted in the E1 region of the virus. The E1 region may then be substituted with the DNA sequences of interest. It was pointed out in a recent article on human gene therapy, however, that "the main disadvantage in the use of adenovirus as a gene transfer vector is that the viral vector generally remains episomal and does not replicate, thus, cell division leads to the eventual loss of the vector from the daughter cells" (Morgan, R. A., et al., *Annual Review of Biochemistry* 62:191–217 (1993)) (emphasis added).

Non-replication of the vector leads not only to eventual loss of the vector without expression in most or all of the target cells but also leads to insufficient expression in the cells that do take up the vector, because copies of the gene whose expression is desired are insufficient for maximum effect. The insufficiency of gene expression is a general limitation of all non-replicating delivery vectors. Thus, it is desirable to introduce a vector that can provide multiple copies of a gene and hence greater amounts of the product of that gene. The present invention overcomes the disadvantages discussed above by providing a tissue-specific, and especially a tumor-specific replicating vector, multiple DNA copies, and thus increased amounts of gene product.

Production of Adenoviral Vectors

Adenoviral vectors for recombinant gene expression have been produced in the human embryonic kidney cell line 293 (Graham, F. L. et al., *J. Gen. Virol.* 36:59–72 (1977)). This cell line, initially transformed with human adenovirus 5, now contains the left end of the adenovirus 5 genome and expresses E1. Therefore, these cells are permissive for growth of adenovirus 2 and adenovirus 5 mutants defective in E1 functions. They have been extensively used for the isolation and propagation of E1 mutants. Therefore, 293 cells have been used for helper-independent cloning and expression of adenovirus vectors in mammalian cells. E1 genes integrated in cellular DNA of 293 cells are expressed at levels which permit deletion of these genes from the viral vector genome. The deletion provides a nonessential region into which DNA may be inserted. For a review, see Young, C. S. H., et al. in *The Adenoviruses*, Ginsberg, H. S., ed., Plenum Press, New York and London (1984), pp. 125–172.

However, 293 cells are subject to severe limitations as producer cells for adenovirus vectors. Growth rates are low. Titres are limited, especially when the vector produces a heterologous gene product that proves toxic for the cells. Recombination with the viral E1 sequence in the genome can lead to the contamination of the recombinant defective virus with unsafe wild-type virus. The quality of certain viral preparations is poor with regard to the ratio of virus particle to plaque forming unit. Further, the cell line does not support growth of more highly deleted mutants because the expression of E1 in combination with other viral genes in the cellular genome (required to complement the further deletion), such as E4, is toxic to the cells. Therefore, the amount of heterologous DNA that can be inserted into the viral genome is limited in these cells. It is desirable, therefore, to produce adenovirus vectors for gene therapy in a cell that cannot produce wild-type recombinants and can produce high titres of high-quality virus.

It is also desirable to control the replication of a therapeutic vector by other than endogenous cellular factors present within the cells to be treated. A high degree of replication could be disadvantageous to the patient, in that vector particles could be released into the bloodstream. This could have toxic side effects in tissues clearing the virus, such as kidneys, liver, lung and spleen, even if the vector does not replicate in non-treated tissue. Furthermore, while current therapeutic vectors have not been shown to replicate at low exposure to normal cells, a high exposure, as potentially caused from a high degree of replication and release of virus at the site of the treated tissue, may cause replication even in normal cells. For example, adenoviruses devoid of E1a, given in a sufficiently high dose, will replicate in normal cells.

Accordingly, it would be highly advantageous to be able to control the level of replication by adding a compound that could dampen replication if replication were excessive.

Another problem in the art is providing more than one gene product controlled by a heterologous regulatory sequence, for example a promoter, on a viral vector (such as cytokines, TK, or other cytotoxic genes, or heat-shock proteins). Thus, in a specific milieu, a particular combination of genes may offer therapeutic advantage. Accordingly, it would be desirable to have several genes in one vector and specifically expressed in the cells to be treated, for example, in a tumor cell. A limitation, however, is that one cannot provide multiple copies of the same promoter to drive each gene, because space would be wasted and the excess nucleotide stretches might not even be accommodated by the virus. Furthermore, during the cloning and replication, homologous recombination could produce deletions between identical promoters and therefore destroy the vector.

SUMMARY OF THE INVENTION

In view of the limitations discussed above, a general object of the invention is to provide novel expression vectors for tissue-specific vector replication and gene expression from the replicating vector.

Accordingly, the invention is directed to an expression vector that contains at least one gene that is essential for replication, which gene is operably linked to a heterologous transcriptional regulatory sequence (heterologous with respect to the gene essential for replication and/or to the vector type), such that an expression vector is created whose replication is conditioned upon the presence of a trans-acting transcriptional regulatory factor(s) that permits transcription from the transcriptional regulatory sequence, or the absence of a transcriptional regulatory factor(s) that normally prevents transcription from that transcriptional regulatory sequence. Thus, these regulatory sequences are specifically activated or derepressed in the target cell or tissue so that replication of the vector proceeds in that cell or tissue and expression of heterologous genes is induced or amplified.

Another object of the invention is to provide an expression vector whose replication, and hence gene expression, can be modulated.

Accordingly, a vector is provided that contains a gene encoding a gene product that can affect the rate and extent of vector replication.

Another object of the invention is to provide a way to coordinate and amplify the expression of multiple genes on a single vector.

Accordingly, an expression vector is provided in which the expression of multiple genes on the vector can be controlled and coordinated through the expression of a gene that is essential for replication, so that the expression of each of the multiple genes is conditional upon vector replication, replication depending upon the tissue-specific expression of the gene product.

Another object of the invention is to provide tissue-specific treatment of abnormal tissue. Thus, a further object of the invention is to provide a method to selectively distribute a vector in vivo in a target tissue, such that a greater number of cells contain the vector than would with a non-replicating vector, and spread of the vector is avoided or significantly reduced in non-target tissue.

Accordingly, a method is provided for selectively distributing a vector in a target tissue, by introducing the replication-conditional vector of the present invention into a target tissue that allows modulatable replication of the vector.

For providing tissue-specific treatment, another object of the invention is to selectively distribute a polynucleotide in a target tissue in vivo.

Accordingly, the invention is directed to a method for selectively distributing a polynucleotide in a target tissue in vivo by introducing the replication-conditional vectors of the present invention, containing the polynucleotide, into the target tissue that allows modulatable replication of the vector. The polynucleotide includes the entire vector or parts thereof, such as one or more heterologous genes.

For providing tissue-specific treatment, a further object of the invention is to selectively distribute one or more heterologous gene products in a target tissue.

Accordingly, the replication-conditional vectors of the present invention are constructed so that they contain one or more heterologous DNA sequences encoding a gene product that is expressed from the vector. When the vectors replicate in the target tissue, effective quantities of the desired gene product are also produced in the target tissue.

Another object of the invention, especially where tissue-specific treatment is involved, is to be able to modulate vector replication, that is, control the level of vector replication. When vector replication proceeds at levels that are undesirable, and particularly levels that may interfere with treatment, an object of the invention is to dampen or decrease the levels of replication by a desired degree. If the levels fall below the desirable amount, an object of the invention is also to be able to allow replication to increase to desirable levels by desired degrees.

Accordingly, the invention provides a method to modulate vector replication during treatment or otherwise (e.g., in producer cells), by providing a gene encoding a gene product that has the ability to interfere with vector replication. When replication is undesirably high, it can be decreased by means of this gene product.

Thus, the invention is further directed to vectors further containing a gene encoding a gene product that can be used to modulate vector replication.

Modulating replication also modulates the expression of heterologous genes contained in the vector. Thus, the expression of such genes can be induced, decreased, increased, or eliminated using the methods and vectors described herein.

Another object of the invention is to provide a method to identify abnormal tissue that can then be treated by the vectors of the present invention. Therefore, a further object of the invention is to identify a tissue in which the replication-conditional vectors of the present invention can be replicated by means of the heterologous transcriptional regulatory sequence contained on the vector so that the tissue can subsequently be treated with the vector, and in which tissue the replication can be modulated.

Accordingly, the invention is further directed to a method wherein the replication-conditional vectors of the present invention are exposed to a given abnormal tissue. If that tissue allows replication and modulation, then replication of the vector will occur and can be detected. Following identification of such a tissue, targeted treatment of that tissue can be effected by tissue-specific transcription and the consequent vector replication in that tissue in vivo.

Thus, a method is provided for assaying vector utility for tissue treatment comprising the steps of removing a tissue biopsy from a patient, explanting the biopsy into tissue culture, introducing a replication-conditional vector into the cells of the biopsy, and assaying for modulatable vector replication in the cells.

Another object of the invention is to provide producer cell lines for vector production. Preferably, the cell lines have one or more of the following characteristics: high titer virus production, resistance to toxic effects due to heterologous gene products expressed in the vector, lack of production of wild-type virus contaminating the virus preparation and resulting from recombination between integrated viral sequences and vector sequences, growth to high density and in suspension, unlimited passage potential, high growth rate, and by permitting the growth of highly deleted viruses that are impaired for viral functions and able to accommodate large pieces of heterologous DNA.

Accordingly, in a further embodiment of the invention, cell lines are provided containing the replication-conditional vector of the present invention, the cells of which allow modulatable replication of the vector or is deficient in a transcription-inhibiting factor(s) that prevents replication of the vector.

In further embodiments of the invention, the cell lines contain nucleic acid copies of the replicated vector. In other embodiments, the cell lines contain virions produced in the cell by replication in the cell of the replication-conditional vector.

In further embodiments, a method is provided for producing a replication-conditional vector or virion comprising the steps of culturing a producer cell line described above and recovering the vector or virion from the cells.

In still further embodiments, a method is provided for producing replication-conditional virions free of wild-type virions or viral vectors free of wild-type vectors, comprising the steps of culturing a producer cell line described above and recovering the replication-deficient virions or vectors from the cells.

In a preferred methods of treatment and diagnosis, the tissue is abnormally proliferating, and especially is tumor tissue. However, the methods are also directed to other abnormal tissue as described herein.

In a preferred embodiment of the invention, the replication-conditional vector is a DNA tumor viral vector.

In a further preferred embodiment, the DNA tumor viral vector is a vector selected from the group consisting of herpesvirus, papovavirus, papillomavirus, parvovirus and hepatitis virus vectors.

In a most preferred embodiment, the vector is an adenovirus vector.

However, it is to be understood that potentially any vector source is useful if it contains a gene essential for replication that can be operably linked to a tissue-specific transcriptional regulatory sequence.

In further methods of treatment and diagnosis, the vector is introduced into the cell or tissue by infection.

Replication can be vector nucleic acid replication alone or can also include virus replication (i.e., virion production). Thus, either DNA or virions or both may be distributed in the target tissue.

In a further preferred embodiment of the invention, a gene in the adenovirus E1 region is operably linked to the tissue-specific heterologous transcriptional regulatory sequence. Preferably, the E1a, E1b or E2a gene is operably linked to the tissue-specific transcriptional regulatory sequence.

In a further embodiment of the invention, the vector encodes one or more heterologous gene products. These heterologous gene products are expressed from the vector replicating in the target tissue. The heterologous gene product may be operably linked to its own promoter or may be operably linked to a transcriptional regulatory sequence from another gene. Regardless, the expression of the heterologous gene product may be controlled by E1a or another transactivator which in turn is regulated by the desired tumor-specific promoter.

In preferred embodiments of the invention, expression of one or more heterologous gene products depends upon expression of the gene essential for replication, which in turn is operably linked to the tissue-specific transcriptional regulatory sequence. Accordingly, when the gene essential for replication is expressed, it causes expression of one or more heterologous gene products, for example by transactivation. In this configuration, such a heterologous gene is activated/induced only when the vector replicates. This is because activation of the tissue-specific regulatory sequence causes expression of the gene product essential for replication which then causes both replication and activation of the expression of the one or more heterologous genes by its transactivation function. Accordingly, not only is expression of the heterologous gene activated, but expression is also amplified because when the vector replicates, each additional copy of the vector also contains a copy of the heterologous gene.

In a highly preferred embodiment, the E1a gene, being operably linked to a heterologous tissue-specific transcriptional regulatory sequence, controls the expression of one or more heterologous genes under the control of promoters that are transactivated by the E1a gene product. Thus, when the E1a gene is expressed, viral replication occurs and gene expression of one or more heterologous genes also occurs. Thus, expression of those genes is controlled at the level of replication and transactivation, such that an expression-amplifying effect is obtained.

In a further embodiment, one or more of the heterologous genes is operably linked to a tissue-specific regulatory sequence, such as the same transcriptional regulatory sequence to which the gene essential for replication is operably linked. Accordingly, the one or more heterologous genes are then activated only in a specific tissue. When the tissue-specific transcriptional regulatory sequence is the same one as that to which the gene essential for replication is operably linked, activation of the one or more heterologous genes occurs only when the vector replicates. Accordingly, as above, the one or more heterologous genes is both activated and amplified.

In other embodiments, the one or more heterologous genes is amplified when the vector replicates but not necessarily activated. This is when these genes are under the control of their own or other constitutive promoters. In this case, there is always a basal level of expression, but when the vector replicates, this expression is amplified because of expression from each new copy of the vector.

In the context of coordinate control (one or more heterologous genes under the control of the same transcriptional regulatory sequence, the same scenario of activation and amplification as discussed above applies.

In a further embodiment, the vector is not used to selectively destroy a cell or tissue type, such as a tumor, but is used to provide a gene product or products at specific levels that are physiologically desirable. An example of such gene product is insulin. Thus, using replication to control gene expression in order to achieve a very specific amount of gene expression is provided by the invention. Accordingly, the vector encodes a gene product which regulates the degree of virus replication, and hence gene expression of other gene products whose amounts must be controlled. An example of such product is one that would inhibit DNA polymerase or nucleotide synthesis. Accordingly, an excess of this product will down-regulate the vector replication. Gene products are also encompassed that will increase the level of vector replication if sufficient gene product is not produced.

Thus, according to the invention, one or more of the heterologous gene products is useful for modulating viral replication. It may directly or indirectly control viral replication as, for example, in the case of thymidine kinase in which viral replication is negatively affected and modulated by the addition of ganciclovir.

With respect to modulating gene expression, the vector provides for modulating the expression of heterologous genes in any of the configurations described above by modulating replication of the vector. This is preferably done via thymidine kinase or a gene product functioning as thymidine kinase does.

In a highly preferred embodiment, the thymidine kinase coding region is operably linked to the E3 promoter in an adenoviral vector. The E1a coding region is under the control of a heterologous tissue-specific promoter. Accordingly, when the tissue-specific promoter is activated, the E1a gene product is produced. This gene product then transactivates the E3 promoter, so that the TK gene is expressed. Further, since the E1a gene activates viral replication, and the E3 gene is not essential for replication, more copies of the viral vector are present to allow greater expression of the TK gene. Ganciclovir can then be added to modulate vector replication. If after adding the ganciclovir, replication falls below a desirable level, the amount of ganciclovir can be decreased to allow an increase in vector replication and so forth, so that desirable levels are permitted within any particular time frame. One example of desirable modulation is to decrease vector replication in a non-target cell.

In a further embodiment of the invention, a heterologous gene product is toxic for the target tissue.

In a further embodiment of the invention, the toxic heterologous gene product acts on a non-toxic prodrug, converting the non-toxic prodrug into a form that is toxic for the target tissue. Preferably, the toxin has anti-tumor activity or eliminates cell proliferation.

In preferred embodiments of the invention, the transcriptional regulatory sequence is a promoter. Preferred promoters include, but are not limited to, CEA, DF3, α-fetoprotein, Erb-B2, surfactant, and especially lung surfactant, tyrosinase promoter, and endothelial-specific promoters. However, any genetic control region that controls transcription of the essential gene can be used to activate (or derepress) the gene. Thus, other genetic control elements, such as enhancers, repressible sequences, and silencers, can be used to regulate replication of the vector in the target cell. The only requirement is that the genetic element be activated, derepressed, enhanced, or otherwise genetically regulated by factors in the host cell and, with respect to methods of treatment, not in the non-target cell.

Preferred enhancers include the DF3 breast cancer-specific enhancer and enhancers from viruses and the steroid receptor family. Other preferred transcriptional-regulatory sequences include NF1, SP1, AP1, and FOS/JUN.

In further embodiments, promoters are not necessarily activated by factors in the target tissue, but are derepressed by factors present in the target tissue. Thus, in the target tissue, repression is lifted.

Transcriptional regulatory factors include, but are not limited to, transactivating factors produced by endogenous viral sequences such as from CMV, HIV, EBV, HSV, SV40, and other such viruses that are pathogenic in mammals and, particularly, in humans.

Methods for making such vectors are well known to the person of ordinary skill in the art. The art adequately teaches the construction of recombinant vectors with deletions or modifications in specific coding sequences and operable linkage to a heterologous transcription control sequence such that expression of a desired coding region is under control of the heterologous transcriptional regulatory sequence. Many viral sequences have been adequately mapped such that it is routine to identify a gene of choice and use appropriate well known techniques (such as homologous recombination of the virus with deleted or otherwise modified plasmids, or ligation of the two) to construct the vectors for tissue-specific replication and expression.

BRIEF DESCRIPTION OF THE FIGURES

FIG. 9A shows that viral plaques are produced by viral genomes containing the AFP promoter operably linked to E1a. FIG. 9B shows that there was no contamination with wild-type virus. FIG. 9C shows that there was no contamination with AV1lacz DNA.

FIG. 10A–F. Tissue specific adenovirus with E1a expressed from the AFP promoter. The experiment shows cytopathic effects and spreading of cell death following infection with the virus AVAFPE1a. FIGS. 10A–10C show uninfected controls in A549.30, A549, and HuH 7 cells, respectively. FIGS. 10D–10F show the results of infection with the virus in A549.30, A549, and HuH 7 cells, respectively.

DETAILED DESCRIPTION OF THE PREFERRED EMBODIMENTS

Definitions

Figure 1A:
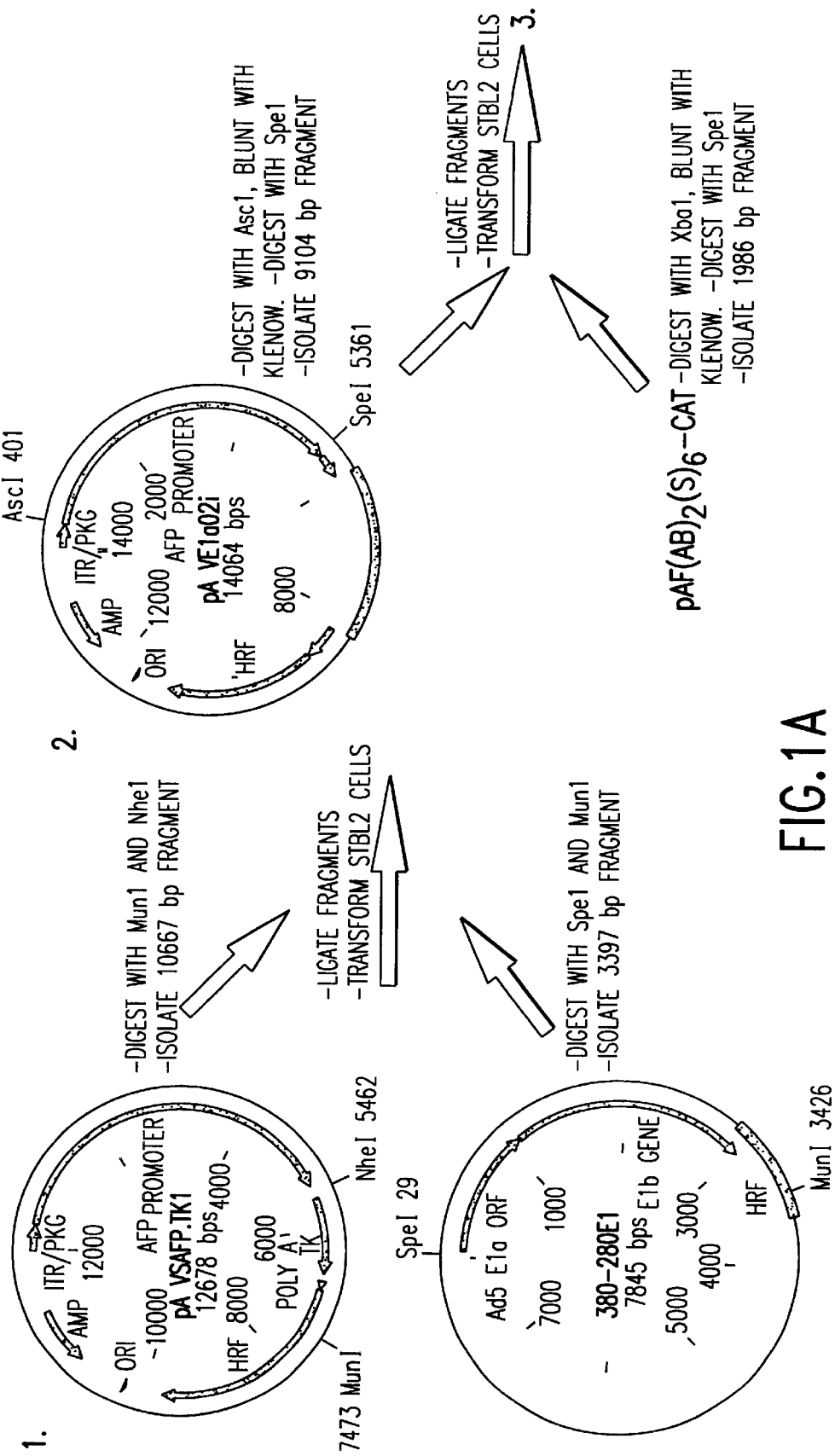
FIG. 1A. Cloning of pAVE1a02i.

The term "abnormally proliferating" is intended to mean a cell having a higher mitotic index than its normally-functioning counterpart, such that there is an abnormal accumulation of such cells.

The term "anti-tumor activity" is intended to mean any activity which inhibits, prevents, or destroys the growth of a tumor.

As used herein, the term "cytotoxic gene" refers to a gene that encodes a protein which either alone or in combination with other agents is lethal to cell viability. Examples of cytotoxic genes which alone are lethal include toxins such as pertussis toxin, diphtheria toxin and the like.

Examples of cytotoxic genes which are used in combination with other agents to achieve cell lethality include, for example, herpes simplex-1 thymidine kinase and cytosine deaminase. The subject is then administered an effective amount of a therapeutic agent, which in the presence of the cytotoxic gene is toxic to the cell. In the specific case of thymidine kinase, the therapeutic agent is a thymidine kinase substrate such as ganciclovir (GCV), 6-methoxypurine arabinonucleoside (araM), or a functional equivalent thereof. Both the thymidine kinase gene and the thymidine kinase metabolite must be used concurrently to be toxic to the host cell. However, in its presence, GCV is phosphorylated and becomes a potent inhibitor of DNA synthesis whereas araM gets converted to the cytotoxic anabolite araATP. Other genes can be used as well in combination with the corresponding therapeutic agent. Such other gene and therapeutic agent combinations are known by one skilled in the art. Another example would be the vector of this invention expressing the enzyme cytosine deaminase. Such vector would be used in conjunction with administration of the drug 5-fluorouracil (Austin and Huber, 1993), or the recently described *E. Coli* DeoΔ gene in combination with 6-methyl-purine-2'-deosribonucleoside (Sorscher et al., 1994).

The term "distributing" is intended to mean the spreading of a vector and its attendant heterologous gene (product) (when present on the vector) throughout a target tissue, and especially throughout abnormally proliferating tissue (non-malignant or malignant). The object of the distribution is to deliver the vector, gene product or the effects of the gene product (as by a bystander effect, for example) to substantially all or a significant number of cells of the target tissue, so as to treat substantially the entire target tissue.

The term "enhancer" is used according to its art-recognized meaning. It is intended to mean a sequence found in eukaryotes and certain eukaryotic viruses which can increase transcription from a gene when located (in either orientation) up to several kilobases from the gene being studied. These sequences usually act as enhancers when on the 5' side (upstream) of the gene in question. However, some enhancers are active when placed on the 3' side (downstream) of the gene. In some-cases, enhancer elements can activate transcription from a gene with no (known) promoter.

The term "functional inactivation" is intended to mean a genetic lesion that prevents the normal activity of a gene product. Thus, functional inactivation could result from a mutation in the gene encoding the gene product. Such a lesion includes insertions, deletions, and base changes. Alternatively, functional inactivation may occur by the abnormal interaction of the normal gene product with one or more other cellular gene products which bind to or otherwise prevent the functional activity of said gene product. Thus, the gene product may be a protein produced from a normal gene but which cannot perform its ordinary and normal function because of an interaction with a second factor.

The term "gene essential for replication" refers to a genetic sequence whose transcription is required for the vector to replicate in the target cell.

The term "gene product" is intended to mean DNA, RNA, protein, peptides, or viral particles. Thus, the distribution, for the purposes of the invention, is of any of these components.

The term "heterologous" means a DNA sequence not found in the native vector genome. Thus, for example, when the vector is based on the adenovirus genome, heterologous DNA sequences are those that are not found in the native adenovirus genome. With respect to a "heterologous transcriptional regulatory sequence," "heterologous" indicates that the transcriptional regulatory sequence is not naturally ligated to the DNA sequence for the gene essential for replication of the vector.

The term "promoter" is used according to its art-recognized meaning. It is intended to mean the DNA region, usually upstream to the coding sequence of a gene or operon, which binds RNA polymerase and directs the enzyme to the correct transcriptional start site.

The term "replication" means duplication of a vector. This duplication, in the case of viruses, can occur at the level of nucleic acid, or at the level of infectious viral particle. In the case of DNA viruses, replication at the nucleic acid level is DNA replication. In the case of RNA viruses, nucleic acid replication is replication into plus or minus strand (or both). In the case of retroviruses, replication at the nucleic acid level includes the production of cDNA as well as the further production of RNA viral genomes. The essential feature is nucleic acid copies of the original viral vector. However, replication also includes the formation of infectious DNA or RNA viral particles. Such particles may successively infect cells in a given target tissue thus distributing the vector through all or a significant portion of the target tissue.

The term "replication-conditional vector" refers to a vector which when introduced into a tissue will not replicate unless a transcriptional regulatory sequence in that vector is activated or derepressed in that tissue. That is, replication depends upon transcription by means of that transcriptional regulatory sequence. Such a vector is replication-conditional as described because it has been modified in the following manner. A gene that is essential for replication has been modified by replacing the transcriptional regulatory sequence on which transcription of that gene normally depends with a heterologous transcriptional regulatory sequence. This transcriptional regulatory sequence depends upon the presence of transcriptional regulatory factors or the absence of transcriptional regulatory inhibitors. The presence of these factors in a given tissue or the absence of such inhibitors in a given tissue provides the replication-conditionality. Accordingly, the native transcriptional regulatory sequence may be replaced with the heterologous transcriptional regulatory sequence. Alternatively, the native transcriptional regulatory sequence may be disabled or rendered dysfunctional by partial removal (deletion) or other mutation (one or more base changes, insertions, inversions, etc.).

The gene sequence may be a coding sequence. It may contain one or more open reading frames, as well as intron sequences. However, such a sequence is not limited to a coding sequence, but includes sequences that are transcribed into RNA, which RNA is itself essential for vector replication. The essential feature is that the transcription of the gene sequences does not depend on the native transcriptional regulatory sequences.

The term "silencer," used in its art-recognized sense, means a sequence found in eucaryotic viruses and eucaryotes which can decrease or silence transcription of a gene when located within several kilobases of that gene.

The term "tissue-specific" is intended to mean that the transcriptional regulatory sequence to which the gene essential for replication is operably linked functions specifically in that tissue so that replication proceeds in that tissue. This can occur by the presence in that tissue, and absence in non-target tissues, of positive transcription factors that activate the transcriptional regulatory sequence. It can also occur by the absence of transcription inhibiting factors that normally occur in non-target tissues and prevent transcription as a result of the transcription regulatory sequence. Thus, when transcription occurs, it proceeds into the gene essential for replication such that in that target tissue, replication of the vector and its attendant functions occur.

As described herein, tissue specificity is particularly relevant in the treatment of the abnormal counterpart of a normal tissue. Such counterparts include, but are not limited to, liver tissue and liver cancer, breast tissue and breast cancer, melanoma and normal skin tissue. Tissue specificity also includes the presence of an abnormal tissue type interspersed with normal tissue of a different tissue type, as for example in the case of metastases of colon cancer, breast cancer, and the like, into tissue such as liver. In this case, the target tissue is the abnormal tissue, and tissue specificity reflects the restriction of vector replication to the abnormal tissue interspersed in the normal tissue. It is also to be understood that tissue specificity, in the context of treatment, is particularly relevant in vivo. However, as described herein, ex vivo treatment and tissue replacement also falls within the concept of tissue specificity according to the present invention.

The term "transcriptional regulatory function" or "transcriptional regulatory factor" is intended to mean any cellular function whose presence activates or represses the heterologous transcriptional regulatory sequence described herein or whose absence permits transcription as a result of the transcriptional regulatory sequences described herein. It is understood that in the given target tissue, a tissue that "lacks the transcriptional regulatory factor" or is "deficient" in the transcriptional regulatory factor could refer to either the absence of the factor or the functional inactivation of the factor in the target tissue.

The term "transcriptional regulatory sequence" is used according to its art-recognized meaning. It is intended to mean any DNA sequence which can, by virtue of its sequence, cause the linked gene to be either up- or down-regulated in a particular cell. In one embodiment of the present invention, the native transcriptional regulatory sequence is completely deleted from the vector and replaced with a heterologous transcriptional regulatory sequence. The transcriptional regulatory sequence may be adjacent to the coding region for the gene that is essential for replication, or may be removed from it. Accordingly, in the case of a promoter, the promoter will generally be adjacent to the coding region. In the case of an enhancer, however, an enhancer can be found at some distance from the coding region such that there is an intervening DNA sequence between the enhancer and the coding region. In some cases, the native transcriptional regulatory sequence remains on the vector but is non-functional with respect to transcription of the gene essential for replication.

Various combinations of transcriptional regulatory sequences can be included in a vector. One or more may be heterologous. Further, one or more may have the tissue-specificity. For example, a single transcriptional regulatory sequence could be used to drive replication by more than one gene essential for replication. This is the case, for example, when the gene product of one of the genes drives transcription of the further gene(s). An example is a heterologous promoter linked to a cassette containing an E1a coding sequence (E1a promoter deleted) and the entire E1b gene. In such a cascade, only one heterologous transcriptional regulatory sequence may be necessary. Thus, a single transcriptional regulatory sequence may drive transcription of the further gene(s) as one mRNA, as the genes are linked by an internal ribosome entry site (IRES). When genes are individually (separately) controlled, however, more than one transcriptional regulatory sequence can be used if more than one such gene is desired to control replication.

The vectors of the present invention, therefore, also include transcriptional regulatory sequence combinations wherein there is more than one heterologous transcriptional regulatory sequence, but wherein one or more of these is not tissue-specific. For example, one transcriptional regulatory sequence can be a basal level constitutive transcriptional regulatory sequence. For example, a tissue-specific enhancer can be combined with a basal level constitutive promoter.

The term "tissue-specific gene regulatory region" or "tissue-specific regulatory region" or "tissue-specific promoter" or "tissue-specific promoter/enhancer" refers to transcription and/or translation regulatory regions that function selectively or preferentially in a specific cell type. Selective or preferential function confers specificity to the gene therapy treatment since the therapeutic gene will be primarily expressed in a targeted or specific cell type. Specific regulatory regions include transcriptional, MRNA maturation signals and translational regulatory regions that are cell type specific. Transcriptional regulatory regions for tumors include, for example, promoters, enhancers, silencers, or artificial control elements added to the vector. Examples are steroid hormone receptor and/or response elements controlled by steriod hormones. Specific examples of such transcriptional regulatory regions for tumors include the promoter/enhancer elements for alpha-fetoprotein, carcinoembryonic antigen and prostate specific antigen. RNA processing signals include, for example, tissue-specific intron splicing signals, whereas translational and regulatory signals can include, for example, mRNA stability signals and translation initiation signals. Thus, specific regulatory regions include all elements that are essential for the production of a mature gene product in a specific cell type.

The invention is particularly directed to neoplastic cells. The neoplastic phenotype is characterized by altered morphology, faster growth rates, higher saturation density, growth in soft agar and tumorigenicity. The therapeutic genes described herein encode proteins which exhibit this activity. "Tumorigenicity" is intended to mean having the ability to form tumors or capable of causing tumor formation and is synonymous with neoplastic growth. "Malignancy" is intended to describe a tumorigenic cell having the ability to metastasize and endanger the life of the host organism. "Hyperproliferative phenotype" is intended to describe a cell growing and dividing at a rate beyond the normal limitations of growth for that cell type. "Neoplastic" also is intended to include cells lacking endogenous functional tumor suppressor protein or the inability of the cell to express endogenous nucleic acid encoding a functional tumor suppressor protein.

The invention can provide tumor-specific replication competent vectors wherein the gene regulatory regions include, but are not limited to alpha-fetoprotein promoter/ enhancer, the carcinoembryonic antigen promoter/enhancer, the tyrosinase promoter/enhancer and the prostate-specific antigen promoter/enhancer. It is to be understood that any regulatory or tumor-specific sequence can be used. For other diseases such as inflammatory conditions, the inducer could be TNF-α and the responding regulatory element the interleukin-6 (IL-6) promoter. The therapeutic gene can encode interleukin-10 (IL-10) or another anti-inflammatory cytokine.

The vectors useful in the methods of this invention can replicate specifically in specific tumor cells. The tumor specificity results from the incorporation of tumor-specific gene regulatory regions which drive the expression of one or more genes which are essential for replication. Such elements include, for example, the alpha-fetoprotein promoter/enhancer, the carcinoembryonic antigen promoter/enhancer, the tyrosine promoter/enhancer and the prostate-specific antigen promoter/enhancer. Each of these gene regulatory regions functions preferentially in specific tumor cell types. For example, the alpha-fetoprotein promoter/enhancer functions preferentially in hepatocellular carcinoma tumor cells. The carcinoembryonic antigen promoter/enhancer functions preferentially in colon cancer and breast tumor cells. The prostate-specific antigen promoter/enhancer functions in prostate tumor cells. The tyrosine promoter enhancer preferentially functions in melanoma tumor cells. Thus, the invention provides for the treatment of cancers including, for example, breast cancer, colorectal cancer, hepatocellular carcinoma and melanoma cancer.

Vectors

The present invention is generally directed to an expression vector capable of expressing one or more heterologous genes in a modulated and tissue-specific mariner wherein a first coding sequence, derived from a gene that is essential for vector replication is operably linked to a tissue-specific transcriptional regulatory sequence, and wherein the vector contains one or more additional heterologous coding sequences.

The first coding sequence for a gene product essential for replication and the tissue-specific transcriptional regulatory sequence are not derived from the same gene (i.e., are heterologous to one another). The tissue-specific transcriptional regulatory sequence, in other words, is not derived from native vector sequences. For example, when the vector is an adenovirus vector, the tissue-specific transcriptional regulatory sequence is not derived from adenovirus.

The additional heterologous coding sequences can be expressed from various locations on the vector. For example, the coding sequence could be linked to the first coding sequence so that expression is directly dependent on transcription from that regulatory sequence through the first coding sequence and then into the additional coding sequence. Alternatively, the additional coding sequence could be expressed by being operably linked to a separate transcriptional regulatory sequence that is activated by the gene product of the first coding sequence (as in transactivation, for example). As a further alternative, the additional coding sequence could be placed under the control of a separate copy of the tissue-specific transcriptional regulatory sequence to which the first coding sequence is linked, although not located in proximity to the first coding sequence. Finally, the additional coding sequence could be, in some instances, transcribed from its native transcriptional regulatory sequence (e.g. promoter) or other different transcriptional regulatory sequence, different from the one to which the first coding sequence is operably linked and not activated by the gene product from the first coding sequence.

Figure 7:
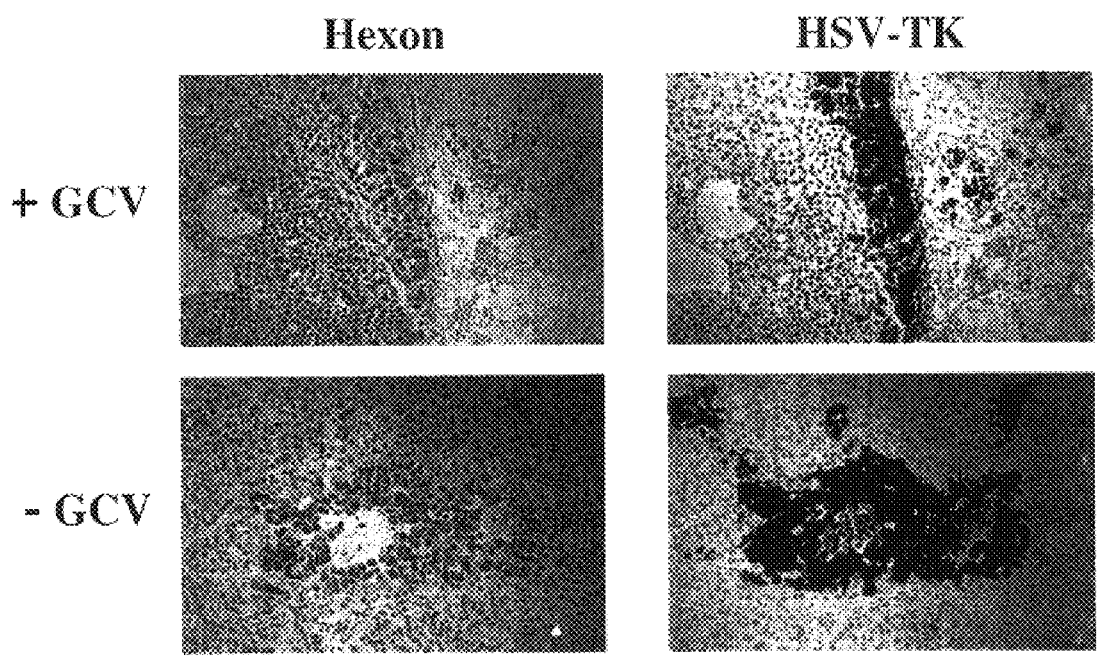
FIG. 7. GCV Inhibition of Av5E1aTk01i Replication In Vivo. Subcutaneous tumors were formed by injecting 1×10$^7$ A549 cells into the subcutaneous space of the right flank of nude mice. After tumors formed 1×10$^9$ pfu of Add1327Tk01i was injected into several animals containing tumors. After 5 days, half of the animals received 5 days of IP GCV treatment at 75 mg/kg once a day. At the end of this time frame all animals were sacrificed. Immunohistochemistry was performed on all samples for HSV-TK expression and hexon expression, the latter which is only expressed when the vector is replicating. Results show as seen in the figure that only hexon is severely diminished when the animals were treated with GCV.
Figure 8:
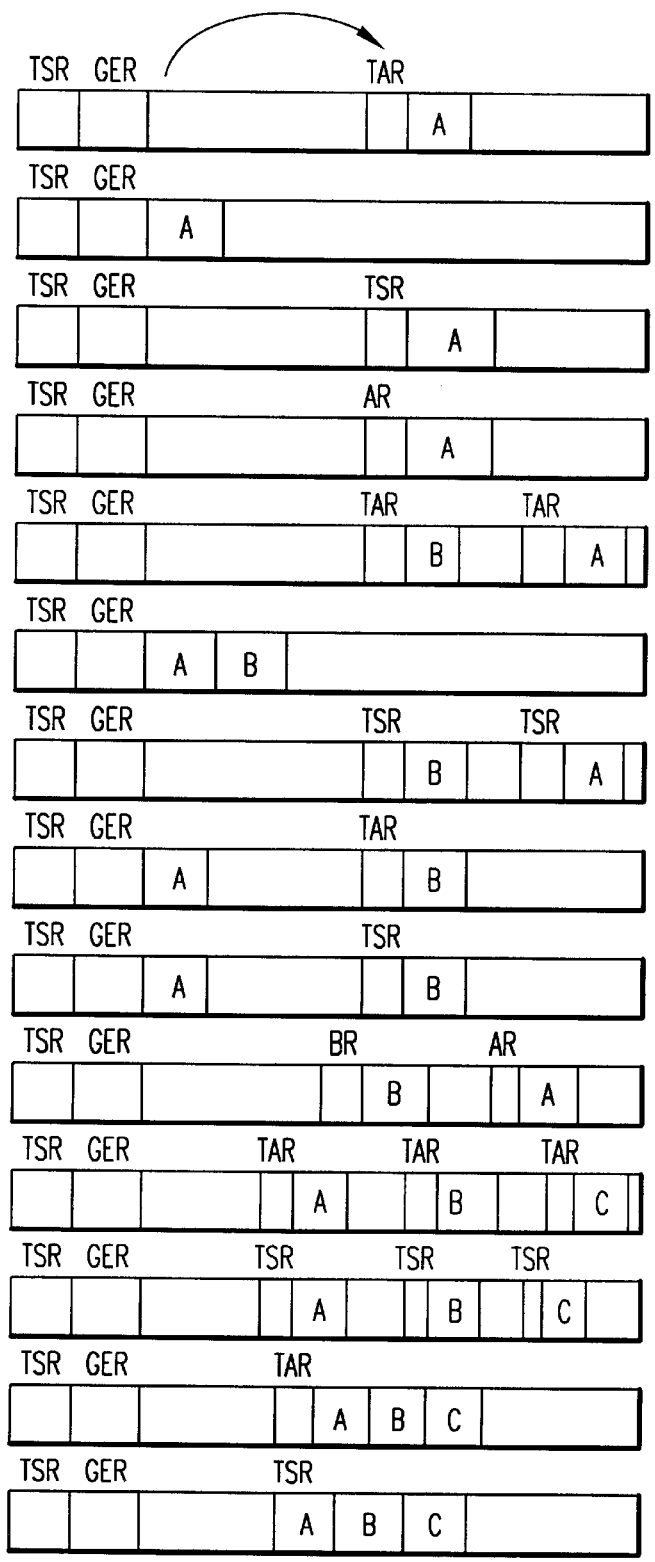
FIG. 8. Diagram of Possible Configurations of Heterologous Genes in Expression Vectors.

When there are multiple heterologous genes expressed, the vector could contain various permutations of the above arrangement. For example, in the case where there is only one additional gene, this gene could be under the control of the same transcriptional regulatory sequence controlling the first coding sequence, under control of a transactivatable transcriptional regulatory sequence, or transcriptionally linked to the first coding sequence so that they are transcribed as a unit from the tissue-specific transcriptional regulatory sequence controlling the first coding sequence, or, finally, under control of another transcriptional regulatory sequence, for example its own native transcriptional regulatory sequence or another constitutive transcriptional regulatory sequence. When a second additional heterologous gene is expressed from the vector, the permutations increase but follow the same general strategy. For example, all three coding sequences can be transcribed from the same unit linked to a single tissue-specific transcriptional regulatory sequence. Alternatively, two of these may be transcribed from the unit and a third transcribed from the same transcriptional regulatory sequence but located in a different proximity. Alternatively, the first coding sequence may be transcribed separately from the second two sequences but both transcribed from the same tissue-specific transcriptional regulatory sequence, etc. Alternatively, the first coding sequence can be used to transactivate the second and third genes, which can be linked under the control of one transcriptional regulatory sequence or under separate transactivatible transcriptional regulatory sequences. FIG. 7 illustrates some of the possible permutations that are encompassed in the present invention. The person of ordinary skill in the art would appreciate the possible permutations even if not explicitly described herein.

In a preferred embodiment, multiple genes on the vector can be controlled through one transactivator. Accordingly, where the first coding sequence has transactivator function, activation at the tissue-specific transcriptional regulatory sequence results in expression in that function and thus transactivation of any genes placed under control of transactivatable transcriptional regulatory sequences at one or more sites in the vector. For example, in an adenoviral-based vector, by linking a heterologous regulatory element to the E1a gene in an otherwise replication competent adenoviral vector, the invention provides the ability to place genes in other transcriptional regulatory sequences, such as E3, E4, E1 regions transactivated by E1a, or multiple copies of these promoters, such as two or more E3 promoters. The design will depend upon the intended use. For example, for cancer therapy a tuimor-specific transcriptional regulatory sequence would be desirable to drive E1a expression while therapeutic genes could be placed under transcriptional regulatory sequences transactivated by E1a, such as one or more E3 promoters, one or more E4 promoters, E1 promoters, or combinations thereof, that contain genes such as HSV-TK, GM-CSF, and IL-2.

In highly preferred embodiments, vectors are designed to express a heterologous gene that is toxic for viral replication. Through this gene one is able to modulate the amount of replication and thus expression of other heterologous gene products, therapeutic or otherwise, for maximal benefit and specificity. For example, in adenoviral vectors having an E1a coding sequence linked to a tissue-specific promoter and having the HSV-TK gene under control of the E3 promoter, replication could be controlled by the addition of ganciclovir.

The preferred vectors of the present invention are adenoviral vectors. In a preferred embodiment of the invention, an adenovirus vector contains a tissue-specific transcriptional regulatory sequence linked to a gene in the E1 region.

In one embodiment, both E1a and E1b are operably linked to heterologous tissue-specific transcriptional regulatory sequences. In an alternative embodiment, only E1a is linked; E1b remains intact. In still another embodiment, E1b is linked, and E1a remains intact or is deleted. In any case, one or more tissue-specific and promoter-specific cellular transcriptional regulatory factors allows virus replication to proceed by transcribing the E1a and/or E1b gene functionally linked to the promoter. Further, either one or both of the E1b functions may be linked to the transcriptional regulatory sequence.

In alternative embodiments, adenovirus vectors are provided with any of the other genes essential for replication, such as E2–E4, under control of a heterologous transcriptional regulatory sequence.

The invention further embodies the use of plasmids and vectors having only the essential regions of adenovirus needed for replication with either E1a, E1b 19 kDa gene, or E1b 55 kDa gene, or some combination thereof, modified. Such a plasmid, lacking any structural genes, would be able to undergo DNA replication. Accordingly, the vectors of the invention may consist essentially of the transcriptional regulatory sequence and one or more genes essential for replication of the vector. In the case of viral vectors, the vectors may consist essentially of the transcriptional regulatory sequence and the gene or genes essential for replication or life-cycle functions of the virus. It is also understood that these vectors may also further consist essentially of a DNA sequence encoding one or more toxic heterologous gene products when such vectors are intended as expression vectors for treatment.

In broader embodiments, the vector is derived from another DNA tumor virus. Such viruses generally include, but are not limited to, Herpesviruses (such as Epstein-Barr virus, cytomegalovirus, *Herpes zoster*, and *Herpes simplex*), papillomaviruses, papovaviruses (such as polyoma and SV40) and hepatitis viruses, parvoviruses, and picornaviruses.

The alternative viruses preferably are selected from any group of viruses in which the essential genes for replication of the virus can be placed under the control of a tissue-specific transcriptional regulatory sequence. All serotypes are included. The only common property of such viruses, therefore, is that they are transducible into target tissue, are genetically manipulatable, and are non-toxic when not replicating.

The relevant viral gene(s) are those that are essential for replication of the viral vector or of the virus. Examples of genes include, but are not limited to, the E6 and E7 regions of human papilloma virus, 16 and 18, T antigen of SV40, and CMV immediate early genes, polymerases from retroviruses and the like. Essentially, these include any gene that is necessary for the life cycle of the virus.

In further embodiments, the vector is derived from an RNA virus. In still further embodiments, the vector is derived from a retrovirus. It is understood, however, that potentially any replicating vector can be made and used according to the essential design disclosed herein.

The vectors described herein can be constructed using standard molecular biological techniques. Standard techniques for the construction of such vectors are well-known to those of ordinary skill in the art, and can be found in references such as Sambrook et al., in *Molecular Cloning. A Laboratory Manual*, Cold Spring Harbor, N.Y. (1989), or any of the myriad of laboratory manuals on recombinant DNA technology that are widely available. A variety of strategies are available for ligating fragments of DNA, the choice of which depends on the nature of the termini of the DNA fragments and can be readily determined by the skilled artisan.

An adenovirus vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a tripartite leader sequence, a multiple cloning site (which may be as herein described); a poly A signal; and a DNA segment which corresponds to a segment of the adenoviral genome. Such DNA segment serves as a substrate for homologous recombination with a modified or mutated adenovirus. The plasmid may also include a selectable marker and an origin of replication. The origin of replication may be a bacterial origin of replication. Representative examples of such shuttle plasmids include pAVS6, as discussed herein and see Trapnell, B. et al., *Adv. Drug Deliv. Rev* 12:185–189 (1994). A desired DNA sequence containing a heterologous gene may then be inserted into the multiple cloning site to produce a plasmid vector.

This construct then is used to produce an adenoviral vector. Homologous recombination then is effected with a modified or mutated adenovirus in which one or more of the native transcriptional regulatory sequences have been deleted and replaced with the desired transcriptional regulatory sequence. Such homologous recombination may be effected through co-transfection of the plasmid vector and the modified adenovirus into a helper cell line by $CaP/O_4$ precipitation.

Through such homologous recombination, a vector is formed which includes adenoviral DNA free of one or more of the native transcriptional regulatory sequences. This vector may then be transfected into a helper cell line for viral replication and to generate infectious viral particles. Transfections may take place by electroporation, calcium phosphate precipitation, microinjection, or through proteoliposomes.

The vector may include a multiple cloning site to facilitate the insertion of DNA sequence(s) containing the heterologous gene into the cloning vector. In general, the multiple cloning site includes "rare" restriction enzyme sites; i.e., sites which are found in eukaryotic genes at a frequency of from about one in every 10,000 to about one in every 100,000 base pairs. An appropriate vector is thus formed by cutting the cloning vector by standard techniques at appropriate restriction sites in the multiple cloning site, and then ligating the DNA sequence containing the heterologous gene into the cloning vector.

The coding sequence whose gene product is essential for vector replication is under the control of a suitable tissue-specific transcriptional regulatory sequence, which may be a promoter or an enhancer. A tissue-specific promoter may be, but is not limited to, AFP, PSA, CEA, DE3, α-fetoprotein, Erb-B2, surfactant, and the tyrosinase promoter. A tissue-specific enhancer may be, but is not limited to, DF3 breast cancer-specific enhancer, enhancers from viruses, and the steroid receptor family.

Suitable promoters for expressing the DNA sequence encoding the heterologous gene product include, but are not limited to, viral promoters, such as the adenoviral major late promoter, cytomegalovirus (CMV) promoter, Rous sarcoma virus promoter, inducible promoters, such as the MMTV promoter, the metallothionein promoter, heat shock promoters, the albumin promoter, the ApoE promoter, and the ApoAI promoter. It is to be understood, however, the scope of the present invention is not limited to specific heterologous genes or promoters.

Suitable native promoters (already located on the viral vector) include, but are not limited to, adenovirus E2, E3 and E4. Further, as discussed, the tissue-specific transcriptional regulatory sequence used to activate vector replication can also be used to control transcription of one or more heterologous genes on locations separate from the first coding sequence in the vector genome.

In one embodiment, the adenovirus may be constructed by using a yeast artificial chromosome (or YAC) containing an adenoviral genome according to the method described in Ketner, et al., *Proc. Nat. Acad. Sci.* 91:6186–6190 (1994), in conjunction with the teachings contained herein. In this embodiment, the adenovirus yeast artificial chromosome is produced by homologous recombination in vivo between adenoviral DNA and yeast artificial chromosome plasmid vectors carrying segments of the adenoviral left and right genomic termini. A DNA sequence containing the heterologous gene then may be cloned into the adenoviral DNA. The modified adenoviral genome then is excised from the adenovirus yeast artificial chromosome in order to be used to generate infectious adenoviral particles.

The infectious viral particles may then be administered in vivo to a host. The host may be an animal host, including mammalian, non-human primate, and human hosts.

The viral particles may be administered in combination with a pharmaceutically acceptable carrier suitable for administration to a patient. The carrier may be a liquid carrier (for example, a saline solution), or a solid carrier, such as, for example, microcarrier beads.

Modulation

For the methods and particularly treatment methods described herein, modulating the amount of vector replication is a highly preferred aspect of the invention. This provides controlled amounts of a heterologous gene product.

The vectors herein provide a method for amplifying the expression of the heterologous gene. In addition to providing constitutive expression of a heterologous gene (as from a native promoter or other transcriptional regulatory sequence or from a tissue-specific promoter in the target tissue), via replication, the vector provides further copies of the heterologous gene for amplified expression. Including a toxic gene on the vector provides a way to control or modulate amplification and thus, expression.

Expression of a gene, particularly a toxic gene, can be absolutely controlled by conditioning the transcription of the gene completely on replication. This is the case when expression of such a gene depends upon transactivation from a gene product produced from a coding sequence of a gene essential for replication operably linked to a tissue-specific transcriptional regulatory sequence.

Vectors expressing gene products, such as HSV-TK, allow the control of replication by drugs such as ganciclovir. This expression in conjunction with tissue-specific control of the expression of a gene essential for replication allows the control of replication by the administration of an external drug. For example, tumor cells can be transduced with a vector expressing E1a in a tissue-specific manner, which vector contains the HSV-TK gene. Upon replication, HSV-TK is either expressed or expression is amplified by replication of the vector. If in the course of monitoring vector replication, there is undesirable spread beyond the tumor edges into surrounding normal tissues, or release into the bloodstream which can be monitored, then viral replication can be dampened by adding ganciclovir to protect the normal cells. At high doses of ganciclovir (for example, 10–50 $\mu$M), replication can be eliminated completely. At lower doses, replication can be dampened. In addition, since E1a expression is dependent upon tissue-specific transcriptional regulatory sequences, in normal cells, E1a expression would be prevented. Therefore, TK expression would also be diminished. Further, in those embodiments in which the TK coding sequence is operably linked to either the tissue-specific promoter or a promoter dependent on E1a transactivation, TK expression should cease entirely.

Also, since most normal cells are not actively dividing, the addition of ganciclovir should shut down viral replication but should not harm cells which would not incorporate this analogue into cellular DNA. Further, even if the cell were dividing, the elimination of TK expression would prevent the phosphorylation of ganciclovir and thus, no deleterious on the cell should result.

In some embodiments, the gene such as TK does not need to be expressed from the vector itself, but can be expressed from an unlinked location such as a separate vector or a cellular genome.

It should be appreciated that the ability to modulate viral replication allows the temporary expression of a given gene, and particularly a cytotoxic gene. This is useful, for example, in a treatment context where temporary expression of a gene is necessary to provide gene therapy. A gene can be expressed at a certain level, maintained at that level, and then expression can be increased and the cell eliminated.

In addition, it may not be desirable to eliminate a cell, but may be desirable to simply express a gene. In this case, it is desirable to express a gene at certain levels. Control of gene expression thus could be effected by a combination of, for example, E1a, TK, and GCV.

Replication and Expression

Expression of heterologous genes and/or treatment thereby are possible using the vectors described herein. Therefore, the invention generally encompasses methods of replicating the vectors described herein.

In preferred embodiments, the methods are specifically directed to the introduction into a target tissue of a replication-conditional adenoviral vector. This vector selectively replicates in the cells of the target tissue. The replication is conditioned upon the function of a transcriptional regulatory sequence to which a viral gene is operably linked, which gene is necessary for vector replication. Thus, in the target tissue, replication can occur because either a cellular function in the target tissue allows transcription. Alternatively, there is a deficiency in a cellular function in the target tissue that normally prevents or inhibits transcription. The presence or absence of such functions provides the selectivity that allows the treatment of a specific tissue with minimun effect on the surrounding tissue(s).

The present invention thus provides methods for selectively distributing a polynucleotide in a given tissue in vivo, significantly reducing or avoiding distribution in non-target tissue. The polynucleotide is provided in the replication-conditional vector which is selectively distributed in the given tissue.

The present invention also provides methods for selectively expressing a gene product in a given tissue, avoiding or significantly reducing expression in non-target or non-tumor tissue. In preferred embodiments, the gene expressed from the vector is a gene that has the potential of being cytotoxic to the host cell and/or toxic to viral replication in the cell. Thus, there is the option of obliterating the cell in which the virus is replicating, or simply decreasing or eliminating viral replication and avoiding cell killing. Accordingly, the invention provides a method for expressing such genes, for example thymidine kinase, in a cell. This provides the possibility of treatment of diseases in which tissue-specific viral replication and gene expression is desired. It also thus provides a method for killing a cell in the case of conditions in which cell killing is desirable, such as cancer and other diseases involving abnormal cellular proliferation such as restenosis.

The invention provides methods for distribution of the above-mentioned vectors to a greater number of target cells than would be reached using a non-replicating vector. Successive infection provides a "domino effect" so that all or substantially all of the cells in the target tissue are reached. Cells in addition to those first exposed to the polynucleotide, vector, or gene product, are thus potentially reached by the methods.

Such treatment is particularly necessary in cases in which surgical intervention is not feasible. For example, in patients with abnormal tissue intimately associated with neural tissue, surgery may be precluded or highly dangerous. Further, in the case of multiple metastases or microscopic metastases, surgery is not feasible.

In the target tissue, DNA replication alone may occur. Late viral functions that result in packaging of vector DNA into virions may also occur.

The vector may be introduced into the target tissue as naked DNA or by means of encapsidation (as an infectious virus particle or virion). In the latter case, the distribution is accomplished by successive infections of cells in the tissue by the virus such that substantially all or a significant number of the daughter cells are infected.

Tissue specificity is particularly relevant with respect to targeting an abnormal counterpart of a particular tissue type while avoiding the normal counterpart of the tissue, or avoiding surrounding tissue of a different type than the abnormal tissue, while treating the abnormal tissue. For example, the vectors of the present invention are useful for treating metastases to the liver. One specific example is colon cancer, which often metastasizes into the liver. It has been found that even when colon cancer metastasizes into the liver, the CEA promoter is active in the cells of the metastases but not in normal liver cells. Accordingly, normal human adult liver should not support replication of a virus that has viral genes essential for replication linked to the colon cancer CEA-specific promoter. Replication should occur in the primary cancer cells. Another example is breast cancer, which also metastasizes to the liver. In this case, the DF3 mucin enhancer is linked to a gene essential for replication such as both E1a and E2a. Replication should occur in breast cancer but not in normal liver. A further example is the α-fetoprotein promoter, which is active in hepatocellular carcinoma. This promoter is linked to a gene essential for replication. It has been found that the promoter is active only in the hepatocellular carcinoma. Accordingly, a virus is used that has a gene essential for replication linked to this promoter. Replication should be limited to hepatocellular carcinoma. A further example is the tyrosinase promoter. This promoter is linked to a gene essential for replication. Replication should occur in melanoma and not in normal skin. In each case, replication is expected in the abnormal but not the normal cells.

In a further embodiment of the invention, the vector encodes a heterologous gene product which is expressed from the vector in the tissue cells. The heterologous gene product can be toxic for the cells in the targeted tissue or confer another desired property.

A gene product produced by the vector can be distributed throughout the tissue, because the vector itself is distributed throughout the tissue. Alternatively, although the expression of the gene product may be localized, its effect may be more far-reaching because of a bystander effect or the production of molecules which have long-range effects such as chemokines. The gene product can be RNA, such as antisense RNA or ribozyme, or protein. Examples of toxic products include, but are not limited to, thymidine kinase in conjunction with ganciclovir.

A wide range of toxic effects is possible. Toxic effects can be direct or indirect. Indirect effects may result from the conversion of a prodrug into a directly toxic drug. For example, *Herpes simplex* virus thymidine kinase phosphorylates ganciclovir to produce the nucleotide toxin ganciclovir phosphate. This compound functions as a chain terminator and DNA polymerase inhibitor, prevents DNA synthesis, and thus is cytotoxic. Another example is the use of cytosine deaminase to convert 5'-fluorocytosine to the anti-cancer drug 5'-fluorouracil. For a discussion of such "suicide" genes, see Blaese, R. M. et al., *Eur. J. Cancer* 30A: 1190–1193 (1994).

Direct toxins include, but are not limited to, diphtheria toxin (Brietman et al., *Mol. Cell Biol.* 10:474–479 (1990)), pseudomonas toxin, cytokines (Blankenstein, T., et al., *J. Exp. Med.* 173:1047–1052 (1991), Colombo, M. P., et al., *J. Exp. Med.* 173:889–897 (1991), Leone, A., et al., *Cell* 65:25–35 (1991)), antisense RNAs and ribozymes (Zaia, J. A. et al., *Ann. N.Y. Acad. Sci.* 660:95–106 (1992)), tumor vaccination genes, and DNA encoding for ribozymes.

In accordance with the present invention, the agent which is capable of providing for the inhibition, prevention, or destruction of the growth of the target tissue or tumor cells upon expression of such agent can be a negative selective marker; i.e., a material which in combination with a chemotherapeutic or interaction agent inhibits, prevents or destroys the growth of the target cells.

Thus, upon introduction to the cells of the negative selective marker, an interaction agent is administered to the host. The interaction agent interacts with the negative selective marker to prevent, inhibit, or destroy the growth of the target cells.

Negative selective markers which may be used include, but are not limited to, thymidine kinase and cytosine deaminase. In one embodiment, the negative selective marker is a viral thymidine kinase selected from the group consisting of *Herpes simplex* virus thymidine kinase, cytomegalovirus thymidine kinase, and varicella-zoster virus thymidine kinase. When viral thymidine kinases are employed, the interaction or chemotherapeutic agent preferably is a nucleoside analogue, for example, one selected from the group consisting of ganciclovir, acyclovir, and 1-2-deoxy-2-fluoro-β-D-arabinofuranosil-5-iodouracil (FIAU). Such interaction agents are utilized efficiently by the viral thymidine kinases as substrates, and such interaction agents thus are incorporated lethally into the DNA of the tumor cells expressing the viral thymidine kinases, thereby resulting in the death of the target cells.

When cytosine deaminase is the negative selective marker, a preferred interaction agent is 5-fluorocytosine. Cytosine deaminase converts 5-fluorocytosine to 5-fluorouracil, which is highly cytotoxic. Thus, the target cells which express the cytosine deaminase gene convert the 5-fluorocytosine to 5-fluorouracil and are killed.

The interaction agent is administered in an amount effective to inhibit, prevent, or destroy the growth of the target cells. For example, the interaction agent is administered in an amount based on body weight and on overall toxicity to a patient. The interaction agent preferably is administered systemically, such as, for example, by intravenous administration, by parenteral administration, by intraperitoneal administration, or by intramuscular administration.

When the vectors of the present invention induce a negative selective marker and are administered to a tissue or tumor in vivo, a "bystander effect" may result, i.e., cells which were not originally transduced with the nucleic acid sequence encoding the negative selective marker may be killed upon administration of the interaction agent. Although the scope of the present invention is not intended to be limited by any theoretical reasoning, the transduced cells may be producing a diffusible form of the negative selective marker that either acts extracellularly upon the interaction agent, or is taken up by adjacent, non-target cells, which then become susceptible to the action of the interaction agent. It also is possible that one or both of the negative selective marker and the interaction agent are communicated between target cells.

In one embodiment, the agent which provides for the inhibition, prevention, or destruction of the growth of the tumor cells is a cytokine. In one embodiment, the cytokine is an interleukin. Other cytokines which may be employed include interferons and colony-stimulating factors, such as GM-CSF. Interleukins include, but are not limited to, interleukin-1, interleukin-1β, and interleukins-2-15. In one embodiment, the interleukin is interleukin-2.

In a preferred embodiment of the invention, the target tissue is abnormally proliferating, and preferably tumor tissue. The vector or virus is distributed throughout the tissue or tumor mass.

All tumors are potentially amenable to treatment with the methods of the invention. Tumor types include, but are not limited to hematopoietic, pancreatic, neurologic, hepatic, gastrointestinal tract, endocrine, biliary tract, sinopulmonary, head and neck, soft tissue sarcoma and carcinoma, dermatologic, reproductive tract, and the like. Preferred tumors for treatment are those with a high mitotic index relative to normal tissue. Preferred tumors are solid tumors, and especially, tumors of the brain, most preferably glioma.

The methods can also be used to target other abnormal cells, for example, any cells which are harmful or otherwise unwanted in vivo. Broad examples include cells causing autoimmune disease, restenosis, and scar tissue formation, abnormal angiogenesis, PRD, arthritis, chronic diabetes, and ARMD.

Further, treatment can be ex vivo. Ex vivo transduction of tumor cells would overcome many of the problems with current viral delivery systems. Tissue is harvested under sterile conditions, dissociated mechanically and/or enzymatically and cultured under sterile conditions in appropriate media. Vector preparations demonstrated to be free of endotoxins and bacterial contamination are used to transduce cells under sterile conditions in vitro using standard protocols. The accessibility of virus to cells in culture is currently superior to in vivo injection and permits introduction of vector viral sequences into essentially all cells. Following removal of virus-containing media cells are immediately returned to the patient or are maintained for several days in culture while testing for function or sterility is performed.

For example, patients with hypercholesterolemia have been treated successfully by removing portions of the liver, explanting the hepatocytes in culture, genetically modifying them by exposure to retrovirus, and re-infusing the corrected cells into the liver (Grossman et al., *Nature Genetics* 6:335–341 (1994)).

Viral transduction also has potential applications in the area of experimental medicine. Transient expression of biological modifiers of immune system function such as IL-2, IFN-γ, GM-CSF or the B7 co-stimulatory protein has been proposed as a potential means of inducing anti-tumor responses in cancer patients.

In broader embodiments, the vector is derived from another DNA tumor virus. Such viruses generally include, but are not limited to, Herpesviruses (such as Epstein-Barr virus, cytomegalovirus, *Herpes zoster*, and *Herpes simplex*), papillomaviruses, papovaviruses (such as polyoma and SV40), and hepatitis viruses.

The relevant viral gene(s) are those that are essential for replication of the viral vector or of the virus. Examples of genes include, but are not limited to, the E6 and E7 regions of human papilloma virus, 16 and 18, T antigen of SV40, and CMV immediate early genes, polymerases from retroviruses and the like. Essentially, these include any gene that is necessary for the life cycle of the virus.

In further embodiments, the vector is derived from an RNA virus. In still further embodiments, the vector is derived from a retrovirus. It is understood, however, that potentially any replicating vector can be made and used according to the essential design disclosed herein.

Diagnostic

It is important to know whether the vectors of the invention will replicate in a specific tissue from a patient. If vector replication is found to be beneficial for therapy, then a screen is provided for those patients who best respond to the therapy disclosed herein. If it is found to be harmful, then there is a screen for prevention of the treatment of patients who would have an adverse response to the treatment. Currently, the only non-biological assays that are commonly used are expression screening, PCR, and sequencing. These often result in false negatives, are time-consuming, expensive, and yield only information in the best of cases about the status of the genes and not their biological function.

Accordingly, a method is provided for identifying an abnormal tissue, the cells of which contain a transcription factor that allows replication of a replication-conditional vector, or are deficient for an inhibitory factor for transcription.

In this method, a tissue biopsy is explanted, a replication-conditional vector is introduced into the cells of the biopsy, and vector DNA replication in the cells is quantitated. Accordingly, a method is provided for screening tissue for the presence of factors that allow vector replication, or for a deficiency of a factor that inhibits transcription. Such a screen is useful, among other things, for identifying tissue, prior to treatment, which will be amenable to treatment with a particular vector to be replicated in the tissue.

Therefore, a method is provided for assaying vector utility for treatment by removing a tissue biopsy from a patient, explanting the biopsy into tissue culture, introducing the replication-conditional vector into the biopsy, and assaying vector replication in the cells of the biopsy.

Testing or screening of tissues includes an assay for vector nucleic acid replication or for virus replication, when the vector is capable of forming infectious virions.

Thus, the invention provides a method for screening a tumor for transcription regulatory functions that allow vector replication or for the absence of these functions which would normally prevent the replication of a virus vector.

However, any abnormal tissue can be screened for the functions described above by an assay for nucleic acid or virus replication.

Producer Cells

In a further embodiment of the invention, a cell is provided which contains a virion produced in the cell by replication in the cell of the replication-conditional vectors of the present invention. Thus, the invention provides "producer cells" for the efficient and safe production of recombinant replication-conditional vectors for further use for targeted gene therapy in vivo.

One of the major problems with the currently available producer cells is that such cells contain, in the genome, viral sequences that provide complementing functions for the replicating vector. Because the cell contains such sequences, homologous recombination can occur between the viral sequence in the genome and the viral vector sequences. Such recombination can regenerate recombinant wild-type viruses which contaminate the vector or virus preparation produced in the producer cell. Such contamination is undesirable, as the wild-type viruses or vectors can then replicate in non-target tissue and thereby impair or kill non-target cells. Therefore, one of the primary advantages of the producer cells of the present invention is that they do not contain endogenous viral sequences homologous to sequences found in the vector to be replicated in the cells. The absence of such sequences avoids homologous recombination and the production of wild-type viral recombinants that can affect non-target tissue.

Accordingly, the invention embodies methods for constructing and producing replication-conditional virions in a cell comprising introducing the replication-conditional vector of the present invention into the cell wherein the genome of the cell is devoid of vector sequences, replicating the vector in the cell, forming the virion, and purifying the virion from the cell. Preferred vectors are DNA viral vectors, including but not limited to herpesvirus, papillomavirus, hepatitis virus, and papovavirus vectors. In preferred embodiments of the invention, the virion is an adenoviral virion and the vector is an adenoviral vector. In further embodiments of the invention, the cell is a tumor cell.

In a further preferred embodiment, the vector encodes a heterologous gene product such that the virion also encodes the gene product, and when the vector or virion are used for gene therapy, the therapy is facilitated by expression of the heterologous gene product. Alternatively, the producer cell can be used for the production of a heterologous gene product per se encoded by the vector. When the vector replicates in the producer cell, the gene product is expressed from the multiple copies of the gene encoding the gene product. Following expression, the gene product can be purified from the producer cells by conventional lysis procedures, or secreted from the producer cell by appropriate secretion signals linked to the heterologous gene by known methods. The transduction of cells by adenoviral vectors has been described. Transfection of plasmid DNA into cells by calcium phosphate (Hanahan, D., *J. Mol. Biol.* 166:577 (1983)), lipofection (Feigner et al., *PNAS* 84:7413 (1987)), or electroporation (Seed, B., *Nature* 329:840 ( ))has been described. DNA, RNA, and virus purification procedures are described (Graham et al., *J. Gen. Virol.* 36:59–72 (1977).

Preferred hosts for producer cell lines include but are not limited to HuH7, SW480, BIGF10, HepG2, MCF-7, and SK-MEL2. Primary tumors from which cell lines can be derived, or existing cell lines, can be tested for the ability to allow replication by means of the tissue-specific transcriptional regulatory sequence. Any primary tumor could be explanted and developed into producer cells for the vectors of the present invention. As long as the cell does not contain endogenous vector or viral sequences that could recombine with the vector or virus to produce wild-type vector or virus, the cell is potentially useful as a host. It is understood that any cell is potentially useful, not only tumor cells.

The ultimate goal for a producer cell line, and particularly an adenoviral producer line, is to produce the highest yield of vector with the least possibility of contamination by wild-type vector. Yield depends upon the number of cells infected. Thus, the more cells that it is possible to grow and infect, the more virus it is possible to generate. Accordingly, candidate cells would have a high growth rate and will grow to a high density. The cell should also have a high amount of viral receptor so that the virus can easily infect the cell. Another characteristic is the quality of the vector produced (i.e., the preparation should not include a high amount of non-infectious viral particles). Accordingly, candidate producer cells would have a low particle-to-plaque-forming-unit ratio. Thus, these cells are a preferred cell type for deriving a producer cell line. Primary explants or the known cell lines can be used.

Thus, such obtainable cells can serve as producer cells for recombinant replication-conditional vectors, viruses, and gene products.

Introduction of Vectors Into Cells

A variety of ways have been developed to introduce vectors into cells in culture, and into cells and tissues of an animal or a human patient. Methods for introducing vectors into mammalian and other animal cells include calcium phosphate transfection, the DEAE-dextran technique, microinjection, liposome mediated techniques, cationic lipid-based techniques, transfection using polybrene, protoplast fusion techniques, electroporation and others. These techniques are well known to those of skill, are described in many readily available publications and have been extensively reviewed. Some of the techniques are reviewed in *Transcription and Translation, A Practical Approach*, Hames, B. D. and Higgins, S. J., eds., IRL Press, Oxford (1984), herein incorporated by reference in its entirety, and *Molecular Cloning*, Second Edition, Maniatis et al., Cold Spring Harbor Laboratory Press, Cold Spring Harbor, N.Y. (1989), herein incorporated by reference in its entirety.

Several of these techniques have been used to introduce vectors into tissues and cells in animals and human patients. Chief among these have been systemic administration and direct injection into sites in situ. Depending on the route of administration and the vector, the techniques have been used to introduce naked DNA, DNA complexed with cationic lipid, viral vectors and vector producer cell lines into normal and abnormal cells and tissues, generally by direct injection into a targeted site.

The aforementioned techniques for introducing polynucleotide, viral and other vectors into cells in culture, in animals and in patients can be used to develop, test and produce, as well as use vectors in accordance with the invention. For instance, cells containing a vector introduced by these methods can be used for producing the vector. In addition, cells containing a vector can be used as producer-cells and introduced into cells or tissues of an animal to produce the vector in situ.

Assay of DNA and Viral Replication

Replication of a polynucleotide, viral or other vector can be assayed by well-known techniques. Assays for replication of a vector in a cell generally involve detecting a polynucleotide, virions or infective virus. A variety of well-known methods that can be used for this purpose involve determining the amount of a labeled substrate incorporated into a polynucleotide during a given period in a cell.

When replication involves a DNA polynucleotide, $^3$H-thymidine often is used as the labelled substrate. In this case, the amount of replication is determined by separating DNA of the vector from the bulk of cellular DNA and measuring the amount of tritium incorporate specifically into vector DNA.

Other methods to assay replication, however, include, but are not limited to, hexon immunohistochemistry or another late gene immunoassay that is linked to DNA or viral replication.

Replication of a polynucleotide vector also may be detected by lysing or permeating cells to release the polynucleotide, then isolating the polynucleotide and quantitating directly the DNA or RNA that is recovered. Polynucleotide replication also may be detected by quantitative PCR using primers that are specific for the assay polynucleotide.

Virions may be assayed by EM counting techniques well known to the art, by isolating the virions and determining protein and nucleic acid content, and by labeling viral genomic polynucleotides or virion proteins and determining the amount of virion from the amount of polynucleotide or protein.

It is well known that virions may not all be viable and where infectivity is important, infectious titer may be determined by cytopathic effect or plaque assay.

Any of these well-known techniques, among others, can be employed to assay replication of a vector in a cell or tissue in accordance with the invention. It will be appreciated that different techniques will be better suited to some vectors than others and to some cells or tissues than others.

Having thus described herein the invention in general terms, the following non-limiting examples are presented to illustrate the invention. Example 1 shows the replacement of the constitutive E1A promoter on an adenoviral vector with a tumor-specific promoter. Constructs made this way have the E1a protein expressed only in tumor cells and therefore, will replicate only in tumor cells.

EXAMPLE 1

The Hepatoma-specific Promoter, α-Fetoprotein Promoter, Linked to E1a

The α-fetoprotein (AFP) promoter has been previously shown to be highly active in hepatoma cells and silent in adult hepatocytes and other adult tissues. A 4.9 kb α-fetoprotein promoter-containing construct was used to derive the promoter. Alternatively, the promoter could also be made based on available references.

pAVE1a02i (FIG. 1A) which places the E1a/E1b genes under the control of the α-fetoprotein promoter in an adenovirus shuttle plasmid was cloned by purifying a restriction fragment which contains the E1a coding region only and all of E1b gene by cleaving the plasmid 380-280E1 (FIG. 1A) with SpeI and MunI and ligating this to pAVSAFP.TK1 (FIG. 1A) cleaved with MunI and NheI.

The adenovirus shuttle plasmid pAVSAFP.TK1 (FIG. 1A), which has the TK gene under the control of the native 4.9 kb α-fetoprotein promoter, was made exactly as described in FIGS. 11 and 12 of U.S. patent application Ser. No. 08/444,284, Chiang et al., "Gene therapy of hepatocellular carcinoma through cancer-specific gene expression," filed on May 18, 1995, which is incorporated herein by reference for its relevant teaching. This shuttle plasmid contains the left ITR, packaging signal, the native AFP promoter, the HSV TK gene, and a homologous recombination fragment. Digestion of this plasmid with MunI and NheI removes the TK gene and part of the E1a gene. What remains is a 10,667 base pair fragment. This fragment is added to the E1a and E1b open reading frames from plasmid 380-280E1 (see below).

Plasmid 380-280E1 contains the E1a ORF and all of E1b. A SpeI/MunI restriction fragment of 3397 base pairs as described in FIG. 1A from plasmid 380-280E1 was used to ligate to the MunI/NheI fragment from pAVSAFP.TK1 to construct pAVE1a02i. The SpeI/MunI fragment from 380-280E1 can be found by reference to plasmid SE280-E1 which contains the same fragment as found in 380-280E1; SE280-E1 can be found in U.S. patent application Ser. No. 08/458,403, incorporated herein by reference for its relevant teaching.

Figure 1B:
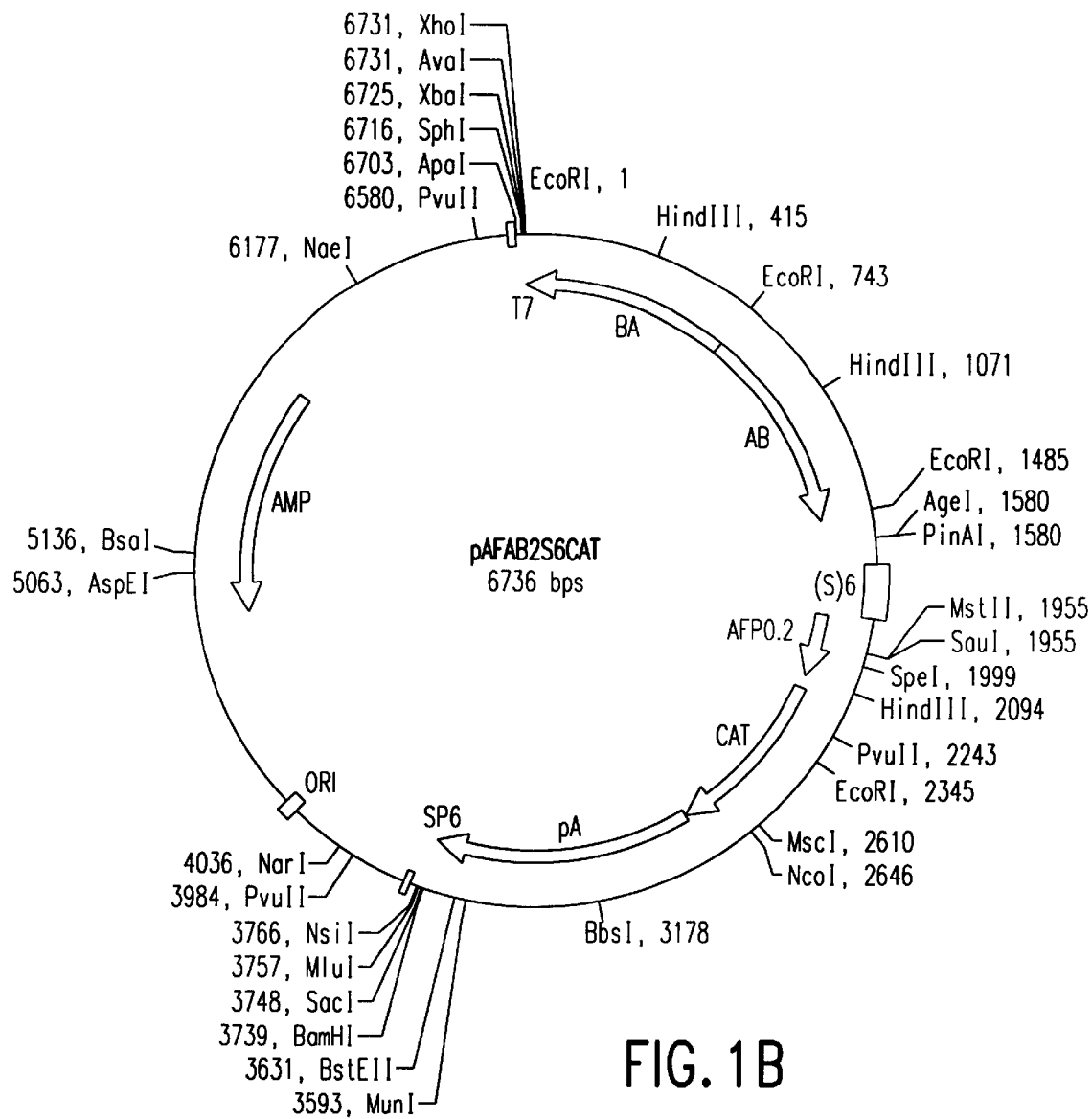
FIG. 1B. Diagram of pAF(AB)$_2$(S)$_6$CAT. The map shows the enhancer regions (AB) in opposite orientation.
Figure 1C:
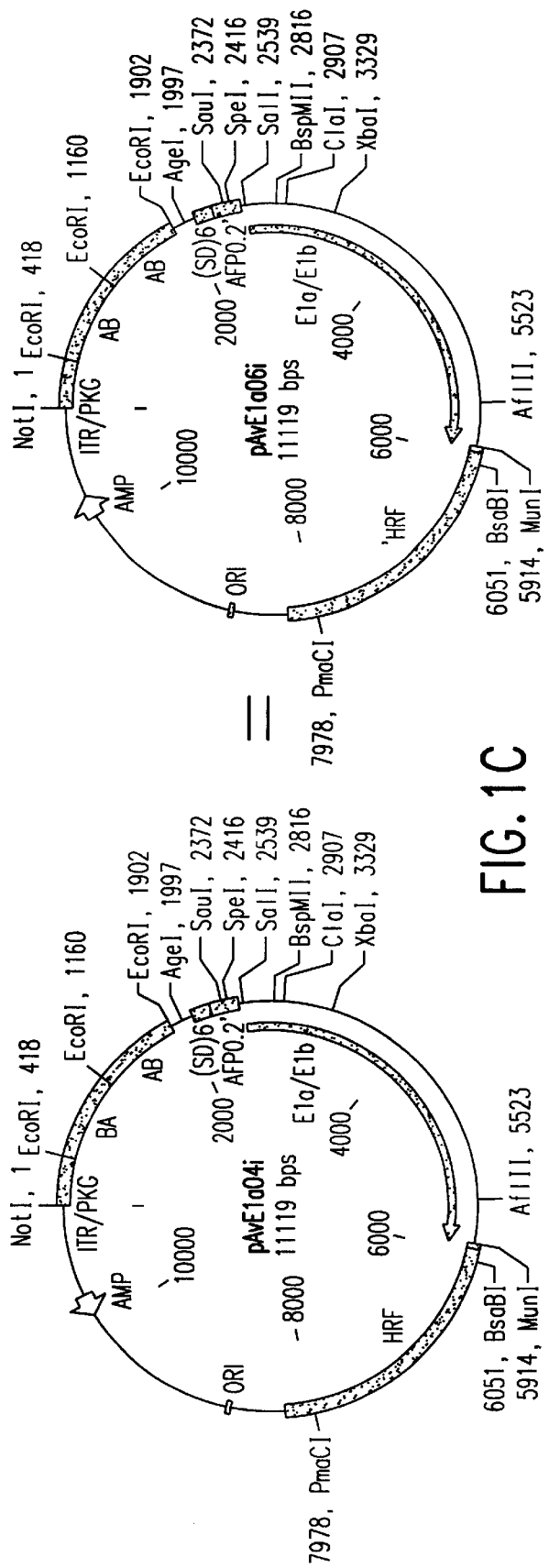
FIG. 1C. Diagram of pAvE1a04i as predicted from a plasmid map and sequence information describing pAF(AB)$_2$(S)$_6$CAT, and pAvE1a06i as determined by restriction digestion mapping and sequencing to be the correct structure.

The shuttle plasmid pAVE1a04i (FIG. 1C) was cloned by digesting pAVE1a02i (FIG. 1A) with AscI followed by DNA polymerase I large fragment (Klenow) filling of the 3' recessed end (FIG. 1A). The linearized pAVE1a02i was then digested with SpeI (FIG. 1A) and the resulting 9104 base pair fragment was isolated by agarose gel electrophoresis. This procedure removes the AFP promoter so that the 9104 base pair fragment contains the above-mentioned components but no promoter.

The plasmid pAF(AB)$_2$(S)$_6$-CAT (FIGS. 1A, 1B) was digested with XbaI followed by Klenow filling of the 3' recessed ends pAF(AB)$_2$(S)$_6$-CAT contains a shortened AFP promoter with six silencer elements and two enhancer regions, AB$_2$ that are responsible for enhancing the activity in hepatoma cells and repressing the activity in adult liver cells.

pAF(AB)$_2$(S)$_6$-CAT was constructed by placing six copies of the distal silencer immediately upstream of the basal 200 base pair AFP promoter. Two copies of the enhancer AB region, originally thought to be in opposite orientation, were placed immediately upstream of the silencer elements. The distal silencer element, the basal promoter, and the enhancer elements are as described in Nakabayashi et al. (*Molec. & Cell. Biol.* 11:5885–5893 (1991)).

The linearized pAF(AB)$_2$(S)$_6$-CAT was then digested with SpeI (FIG. 1A) and the 1986 base pair fragment containing the shortened AFP promoter was isolated by gel electrophoresis. The 9104 base pair fragment of pAvE1a02i and the 1986 base pair fragment of pAF(AB)$_2$(S)$_6$-CAT containing the shortened synthetic AFP promoter, were ligated to make the plasmid pAvE1a04i (FIG. 1C) which places the adenovirus E1a gene under the control of the shortened AFP promoter.

The pAF(AB)$_2$(S)$_6$-CAT was reported to have two copies of the enhancer AB region in opposite orientation but was determined by the inventors to have the enhancer region as a tandem repeat. The plasmid map of pAvE1a04i shows the enhancer (AB) region of the AFP promoter as an inverted repeat (FIG. 1A). However, the map was later corrected to show the true orientation of the enhancer regions. The corrected plasmid map was designated as pAvE1a06i.

Figure 2A:
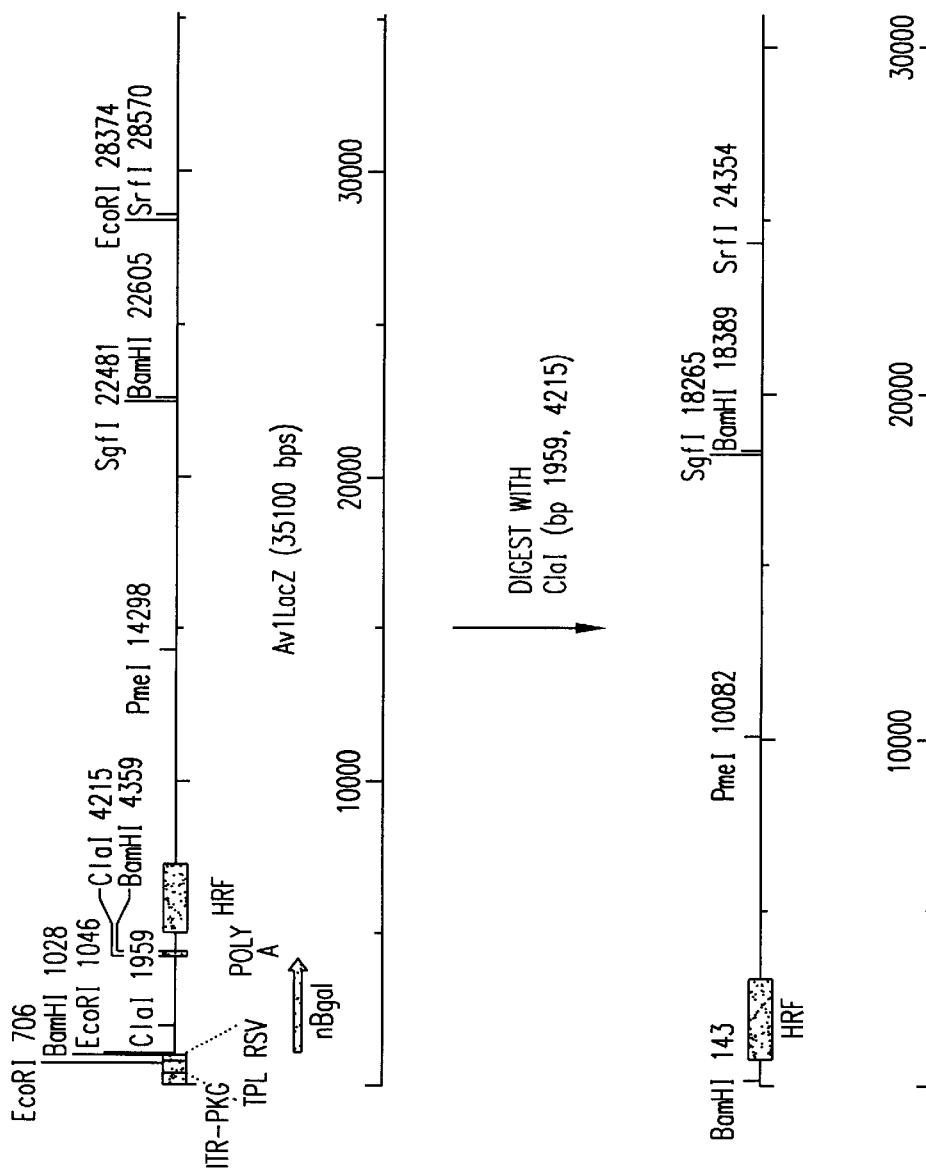
FIG. 2A. Diagram of ClaI digestion of Av1LacZ.
Figure 2B:
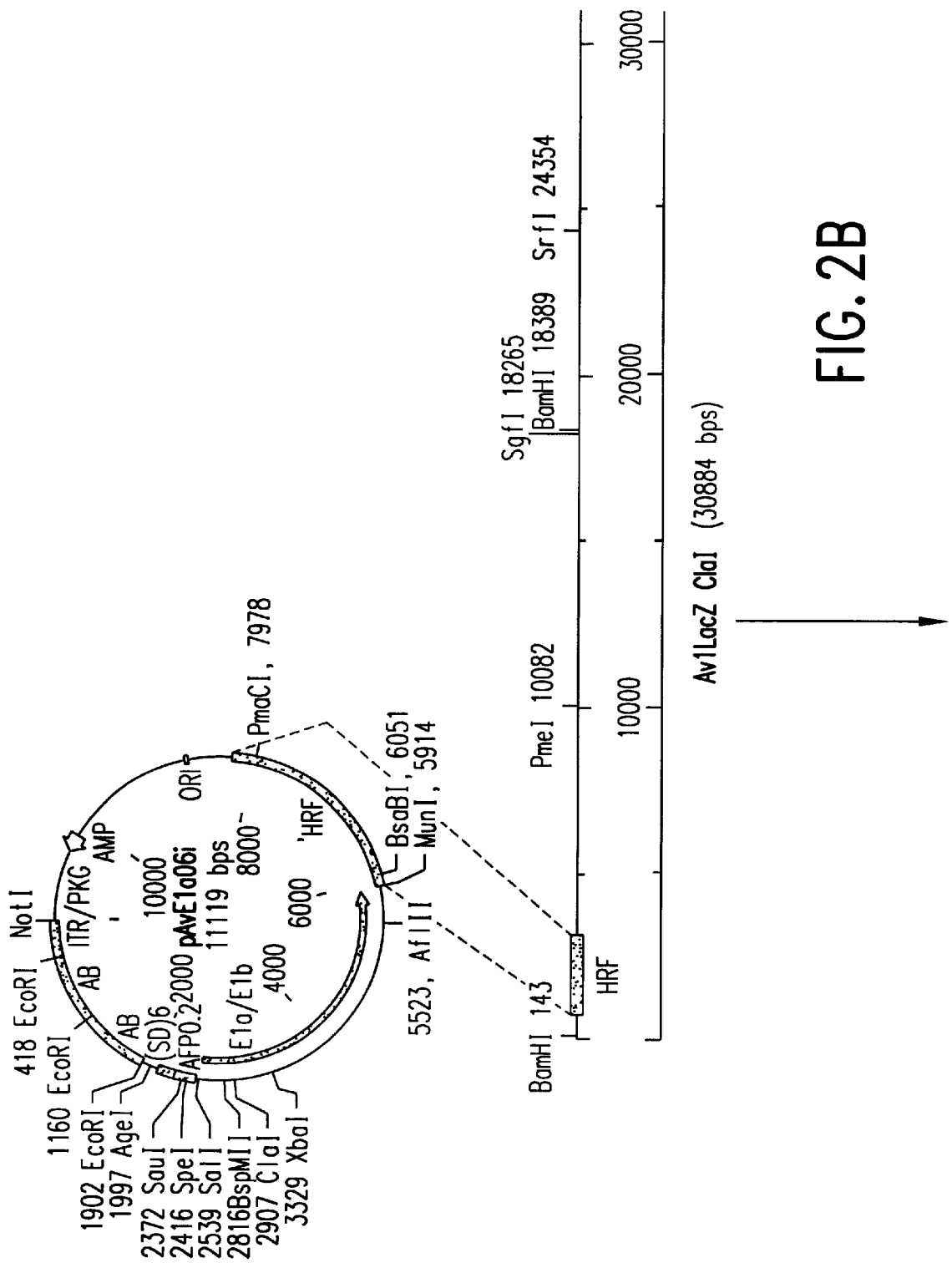
FIG. 2B. Diagram of co-transfection of 293 cells with pAvE1a06i and Av1LacZ ClaI digest (30,884 bp), to produce AvE1a06i.
Figure 2C:
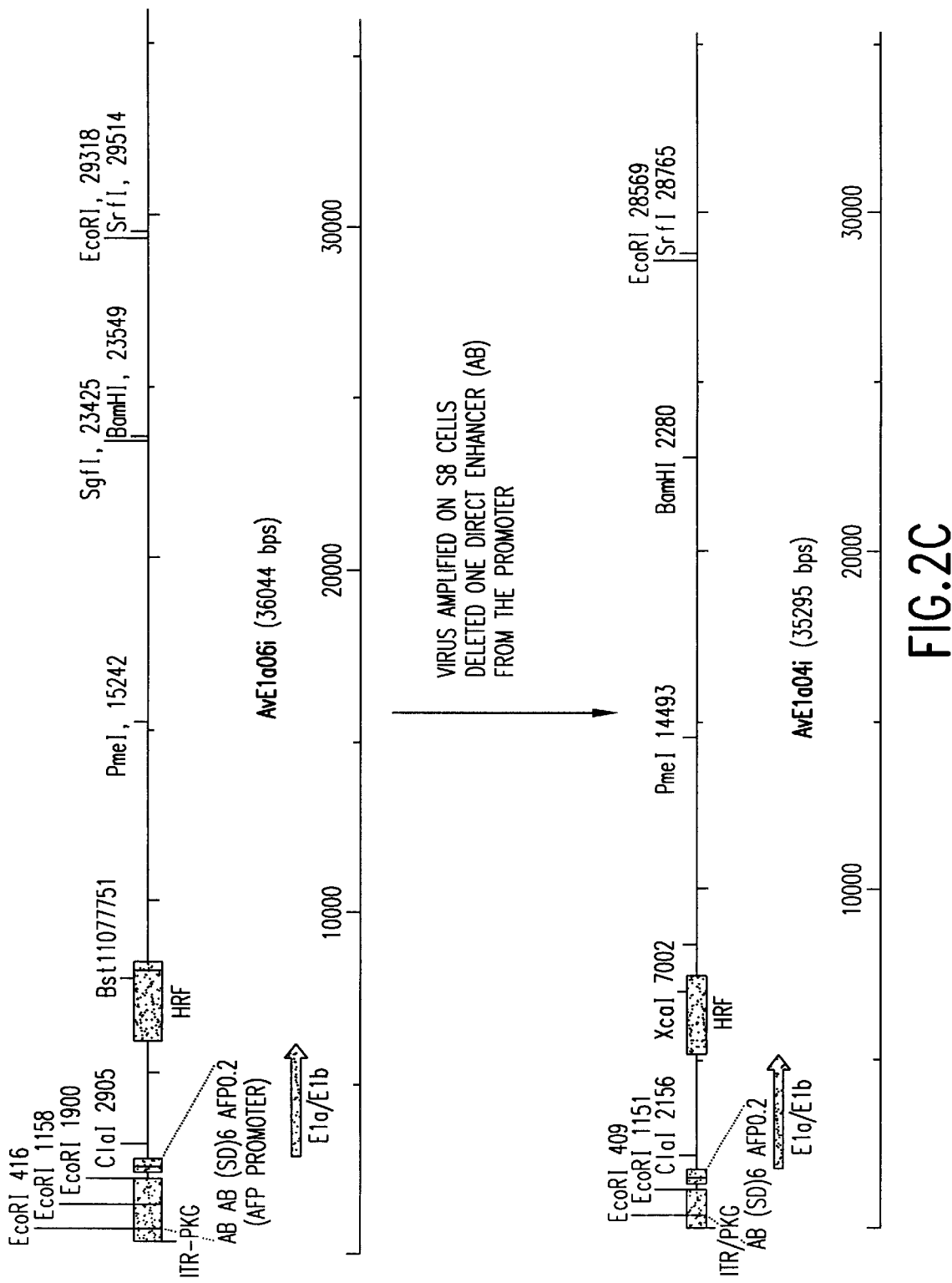
FIG. 2C. Amplification of AvE1a06i virus on S8 cells deleted one direct enhancer (AB) from the promoter. The new construct is designated AvE1a04i.

Construction of a Virus With the Hepatoma-specific AFP Promoter Operably Linked to the E1a Gene The adenovirus AvE1a04i (FIG. 2C) was constructed by homologous recombination of the shuttle plasmid, pAvE1a06i (see FIGS. 1C and 2B), with the large (ClaI) fragment of Av1lacZ DNA (FIG. 2A) in 293 cells. Resulting recombinant virus containing the AFP promoter with the two direct repeat enhancers was isolated and initially designated as AvE1a06i (FIG. 2C, top of page). In the process of plaque purifying the recombinant virus, a single enhancer deletion mutant was isolated and designated as AvE1a04i (FIG. 2C, bottom of page).

AvE1a04i was shown to replicate specifically in cell lines as described in PCT App. No. US 95/15455 (U.S. Pat. No. 5,998,205).

The plasmid pAVE1a04i was grown in STBL2 cells and was purified by standard cesium banding methods prior to use in transfection. Genomic AV1lacZ4 DNA was isolated from cesium gradient-purified virus (herein described). The AV1lacZ4 purified virus was digested with proteinase K and the DNA isolated by phenol/chloroform extraction. The purified DNA was digested with ClaI and the large fragment was isolated by gel electrophoresis and quantified. 5 μg of the plasmid pAVE1a04i and 2.5 μg of the large ClaI fragment of AV1lacZ4 were co-transfected into 293 cells using a calcium phosphate-mediated transfection procedure (Promega, E1200 kit). The transfection plate was overlayered with a 1% agarose overlay and incubated until plaques formed. Once plaques had formed, they were picked and the virus was released into 500 μl of IMEM media by alternate cycles of freezing and thawing (5×). The eluted viral plaques were reamplified on A30 cells for 48 hours and then the cells were lysed for use in screening by PCR.

Figure 9A:
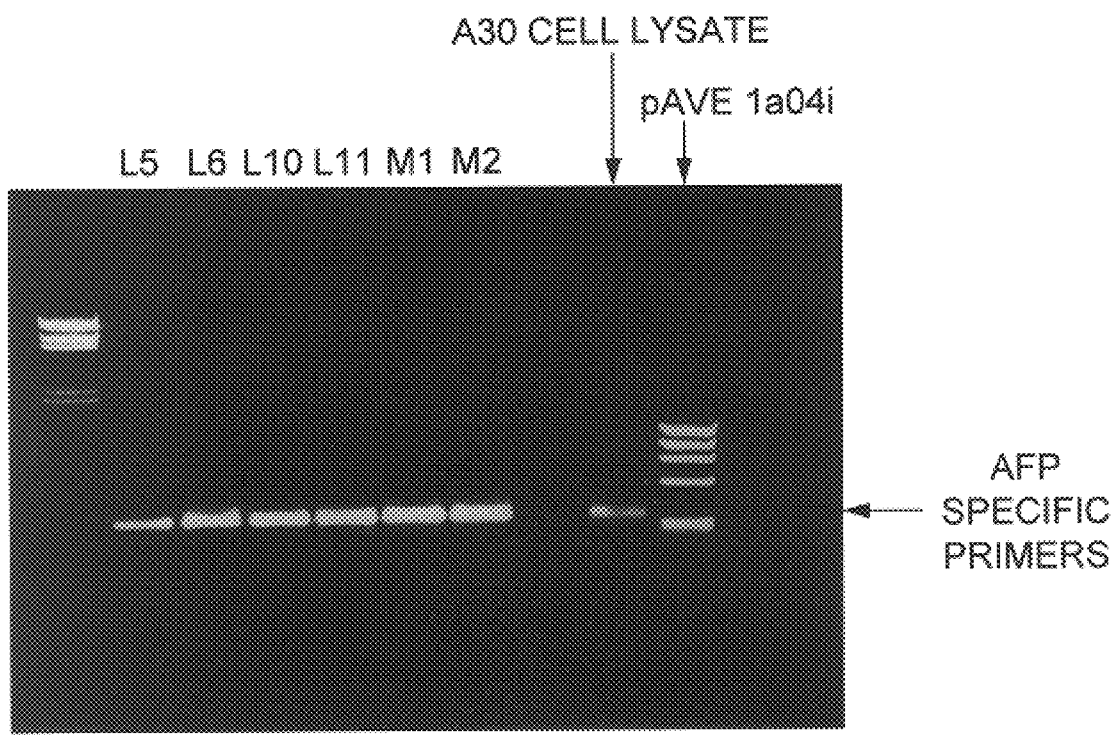
FIG. 9A–C. PCR identification of recombinant adenovirus with E1a expressed from the hepatoma-specific AFP promoter.
Figure 9B:
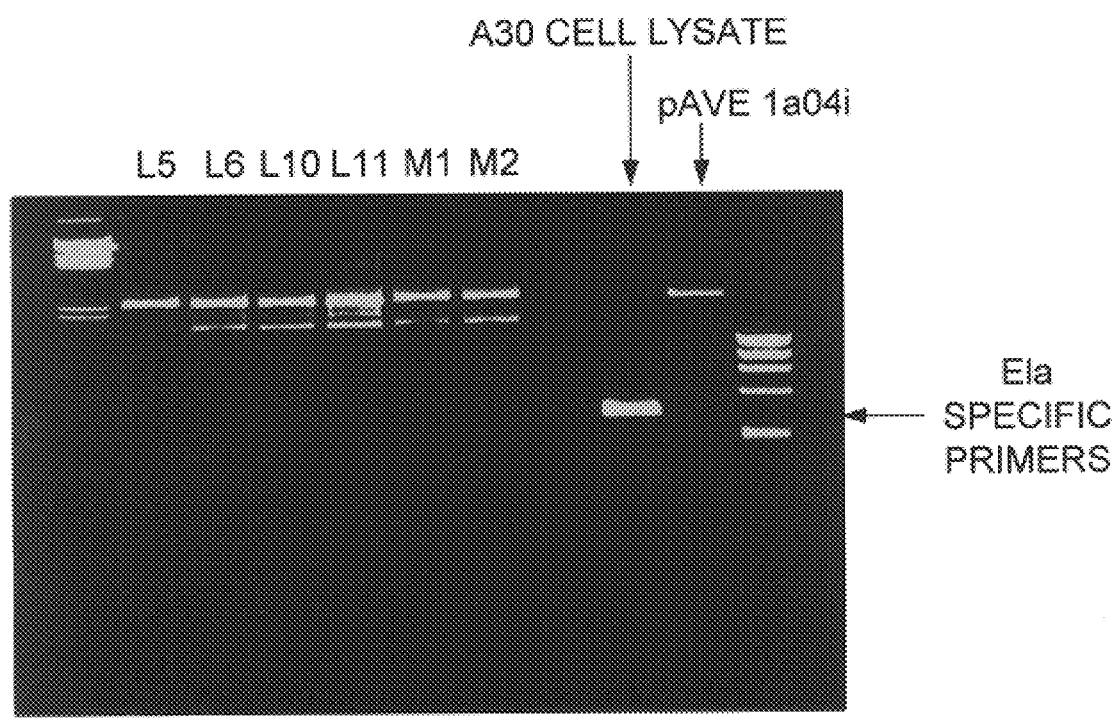
Figure 9C:
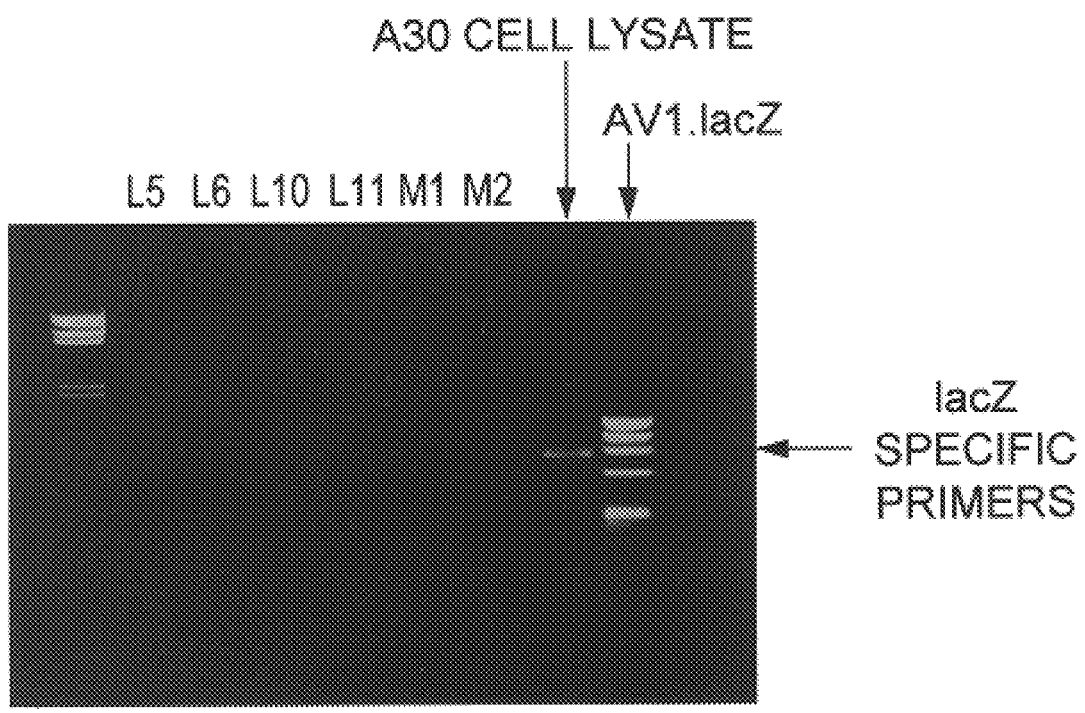

Primers specific for the short AFP (sAFP) promoter in plasmid pAVE1a04i were used to identify the putative plaques. FIG. 9A shows that viral plaques contain a sAFP-specific band of the predicted molecular weight and specific for the sAFP primers. To confirm that this recombinant virus was not contaminated with Ad5d1327 (wild type), E1a primers were used. FIG. 9B demonstrates that no wild type virus was present and that pAVE1a04i plasmid sequences were present in the recombinant virus. FIG. 9C demonstrates that little or no AV1lacZ4 was present. The data indicate the construction of a virus with E1a under control of a tissue-specific promoter and that the virus is capable of replication in A30 cells.

Individual plaques were grown in A30 cells and analyzed by PCR for the presence of the AFP promoter (FIG. 9A). The arrow indicates the AFP-specific band generated from PCR. The figure shows that the band is present in each of the viruses in the selected plaques (L6, L10, L11, M1 and M2). The control in the experiment was an A30 cell lysate, expected not to contain the band. The experiment also included the PCR reaction with the plasmid pAVE1a04i (the shuttle plasmid from which the virus was made and which therefore should produce the AFP-specific fragment). Thus, FIG. 9A confirms the presence of a recombinant virus containing the AFP promoter. FIGS. 9B and 9C confirm that these results were not the result of contamination in the individual plaques. FIG. 9B uses E1a-specific primers to detect the presence of any contaminating wild-type virus. The arrow shows the band produced with E1a-specific primers. The figure shows that none of the recombinant viruses produced the relevant band. FIG. 9C confirms that there is no AV1.lacZ contamination in the viral plaques (since the viruses were made using AV1.lacZ DNA). The figure indicates that only the lane containing AV1.lacZ DNA produced the band.

Tissue-specific Viral Replication

Figures 10A, 10B, 10C, 10D, 10E, 10F:
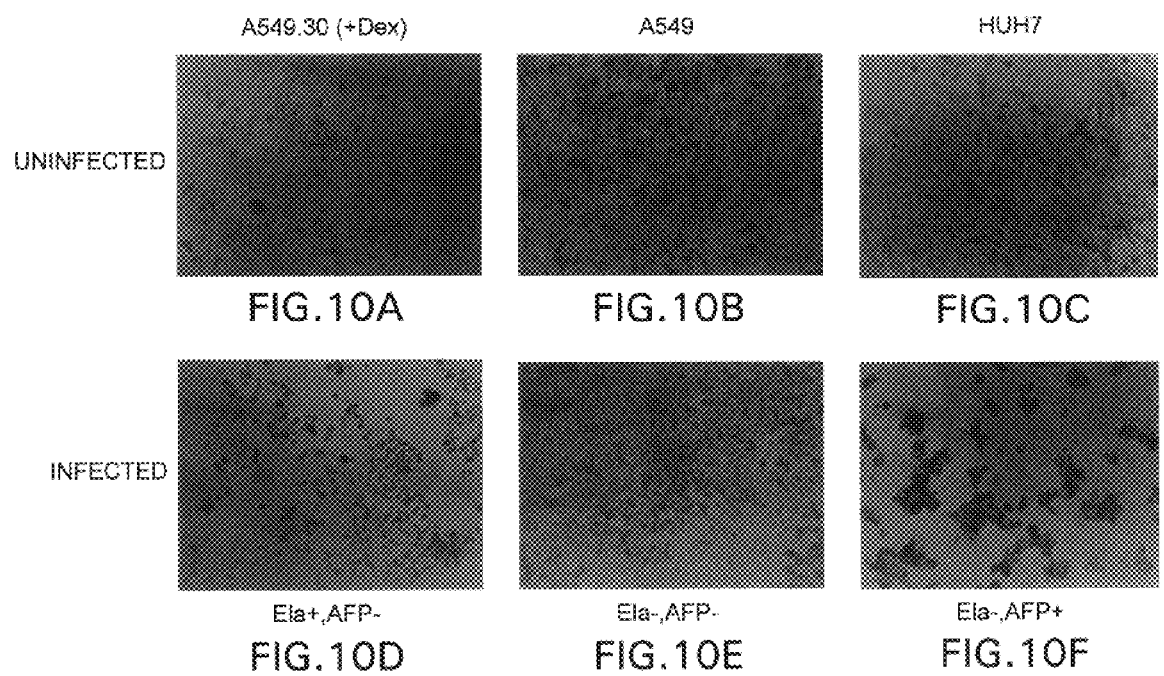

Cytopathic viral lysate of this virus ("AVAFPE1a") was serially diluted in logs of 10 on A549.30 cells, A549 cells, and HuH 7 cells. A549.30 cells express the E1a from the glucocorticoid receptor element (GRE) promoter in the presence of dexamethasone since this construct is integrated into the genome of this cell line. Thus, any E1a-deleted virus or any virus not expressing E1a should be able to replicate in this cell line. This has previously been shown for E1-deleted vectors (unpublished communication). As can be seen from FIGS. 10A and 10D, the AVAFPE 1a vector replicates in the infected cells as indicated by characteristic cytopathic effects and spreading of cell death. The A549 cells do not express AFP and should not be capable of transactivating the AFP promoter. In addition, A549 cells do not express E1a. Thus, AVAFPE1a should not be able to replicate in this cell line. As can be seen from FIGS. 10B and 10E, both uninfected and infected wells appear identical with no characteristic cytopathic effects or spreading observed at all dilutions tested. HuH 7 cells do express AFP, should transactivate the AFP promoter, and should make E1a with subsequent replication. As shown in FIGS. 10C and 10F, AVAFPE1a clearly replicates, as indicated by the cytopathic effects. In addition, on several wells of infected HuH 7 cells, the replication began with a single plaque which spread throughout the rest of the well within one week. All HuH 7 wells showing cytopathic effects were tested by PCR and demonstrated to be free of wild-type virus and AV1LacZ4 virus, and to contain an intact AFP promoter. These data clearly indicate that a virus has been constructed that is capable of replicating specifically in tumor cells expressing AFP.

The Breast Cancer-specific DF3-Mucin Enhancer

The DF3 breast carcinoma associated antigen (MUC1) is highly overexpressed in human breast carcinomas. The expression of the gene is regulated at the transcriptional level. The DNA sequence between −485 −588 is necessary and sufficient for conferring a greater than 10-fold increase in transcription of the reporter gene CAT when placed immediately upstream of a basal promoter derived from the Herpesvirus TK promoter in transient transfection assays performed in the human breast cancer cell line MCF-7. A specific transcription factor which binds to this region of DNA has also been found within cells derived from the breast cancer cell line MCF-7 but not a non-breast cancer cell line HL-60. The same region of DNA has been found to promote breast cancer-specific expression of the TK gene in the context of a retroviral construct or an adenoviral construct.

The DF3 enhancer from −598 to −485 (obtained from GenBank) was synthesized by constructing four oligonucleotides synthesized in such a way as they would overlap and anneal. The oligonucleotides are shown in Table 1. Additional restriction sites were added on both ends for future ease of cloning. One end was kept blunt to enable cloning into the SmaI site of the vector pTK-Luc. This vector contains the basal promoter of the Herpesvirus TK gene which gives low level basal activity in a variety of cells. It was used as a source of this basal promoter. The other end had an overlapping BglII site for ease in cloning into the BglII site of pTK-Luc. 1,000 ng of each oligonucleotide were annealed in 0.017 M Tris, pH 8.0, 0.16 M NaCl in a total volume of 26.5 µl by heating at 95° C. for two minutes and allowing to cool to room temperature after several hours. Finally, 1 µl of this mixture was ligated to 100 ng of previously SmaI/BglII-and glass milk (BIO 101)-purified vector by standard conditions. Following transformation into DH5 cells (GIBCO), colonies were screened for the presence of the insert by standard restriction digests. DNA derived from this vector is then cleaved with HindII and blunted by Klenow. It is then cleaved by AscI. This fragment, which contains the DF3 enhancer lined to the basal TK promoter, is then purified by agarose gel electrophoresis and glass milk and ligated to the plasmid pAVE1a02i, cleaved with SpeI and blunt-ended with AscI and purified as above. The resultant plasmid has the E1A gene product under the control of the DF3 enhancer and basal TK promoter and is in an adenoviral shuttle plasmid. 5 µg of this plasmid, pAVE1a03i, is cotransfected with 5 µg of the right ClaI fragment arm, derived from Add1327, into 293 cells. Plaques are screened for the expected recombinant virus by standard methods.

A crude virus lysate is used to infect MCF-7 at an MOI of 10. Virus stocks are confirmed to replicate specifically in breast cancer cells by standard methods. Virus is scaled up in MCF-7 cells and/or 293 cells as described for scaleup and purification on 293 cells. Virus stocks are tested for replication in vivo by using a mode mouse model of MCF-7 and, as a negative control, a cervical cancer (Hela) derived tumor is used. Virus is tested for a recombinational event in 293 cells which would generate a wild-type virus by PCR assay of the original EIA promoter which would only be in a wild-type virus. A variety of other human and rat breast cancer cell lines and non-related cell lines are also tested. The TK gene can be inserted into the E3 region and have TK driven either by the E1A-dependent promoter present there or under the control of the RSV or CMV promoter.

The Melanoma-specific Tyrosinase Promoter

PCR primers and PCR were used to clone a fragment of DNA 800 bp upstream of the tyrosinase gene from mouse genomic DNA using PFU and the described primers as described by Stratagene. The resultant PCR fragment was cloned into pCRSCRIPT and then recloned into pAVE1a02i by digesting the new plasmid with AscI/SpeI and pAVE1a01i with AscI/SpeI and ligating the two together. The final shuttle plasmid, pAVE1a04i, which has E1a/E1b under the control of the tyrosinase promoter, is utilized to make a recombinant virus identically as described above.

The Colon Cancer-specific CEA Promoter

The CEA promoter was cloned from human genomic DNA as described above and cloned in a similar way into the pAVE1a01i plasmid using the primers shown in Table 1. The final shuttle plasmid, pAVE1a05i, is used to generate recombinant virus as described above.

Replacing the Promoter of E2a on an Adenoviral Vector With a Tumor Specific Promoter Constructs made as above will have the E2a protein (essential for viral replication expressed only in tumor cells.

Therefore, replication of the vector occurs only in tumor cells. All four of these very specific promoters (in the examples above) are used to place the E2a coding region obtained from pSE280-E2a (see U.S. patent application to Kayden et al., "Improved adenoviral vectors and producer cells" filed Jun. 2, 1995) under the control of that tumor-specific promoter. The resultant plasmid is recombined with Add1327, using standard methods of homologous recombination. The final virus is grown in the cell lines described in the aforementioned patent application or in the tumor specific cell lines. The E2a protein, because it is needed in stoichiometric amounts, has the ability to regulate the degree of replication over a broad range. This is desirable for therapy. The methods used are the same as those described for E1a. The difference is that a shuttle plasmid is used that places E2a under the control of the tumor specific promoter and returns it to a virus backbone (by homologous recombination) that has the E2a and E3 genes deleted.

Replacement of Other Therapeutic Toxic Genes Into the Tumor-specific Replication Competent Vectors Genes such as TK, cytokines, or any therapeutic genes can be placed into the E3 region of the vector backbone by standard plasmid construction and homologous recombination. Those genes can be placed under the control of an E1a-dependent promoter, or a constitutive promoter such as RSV or CMV.

EXAMPLE 2

Figure 3A:
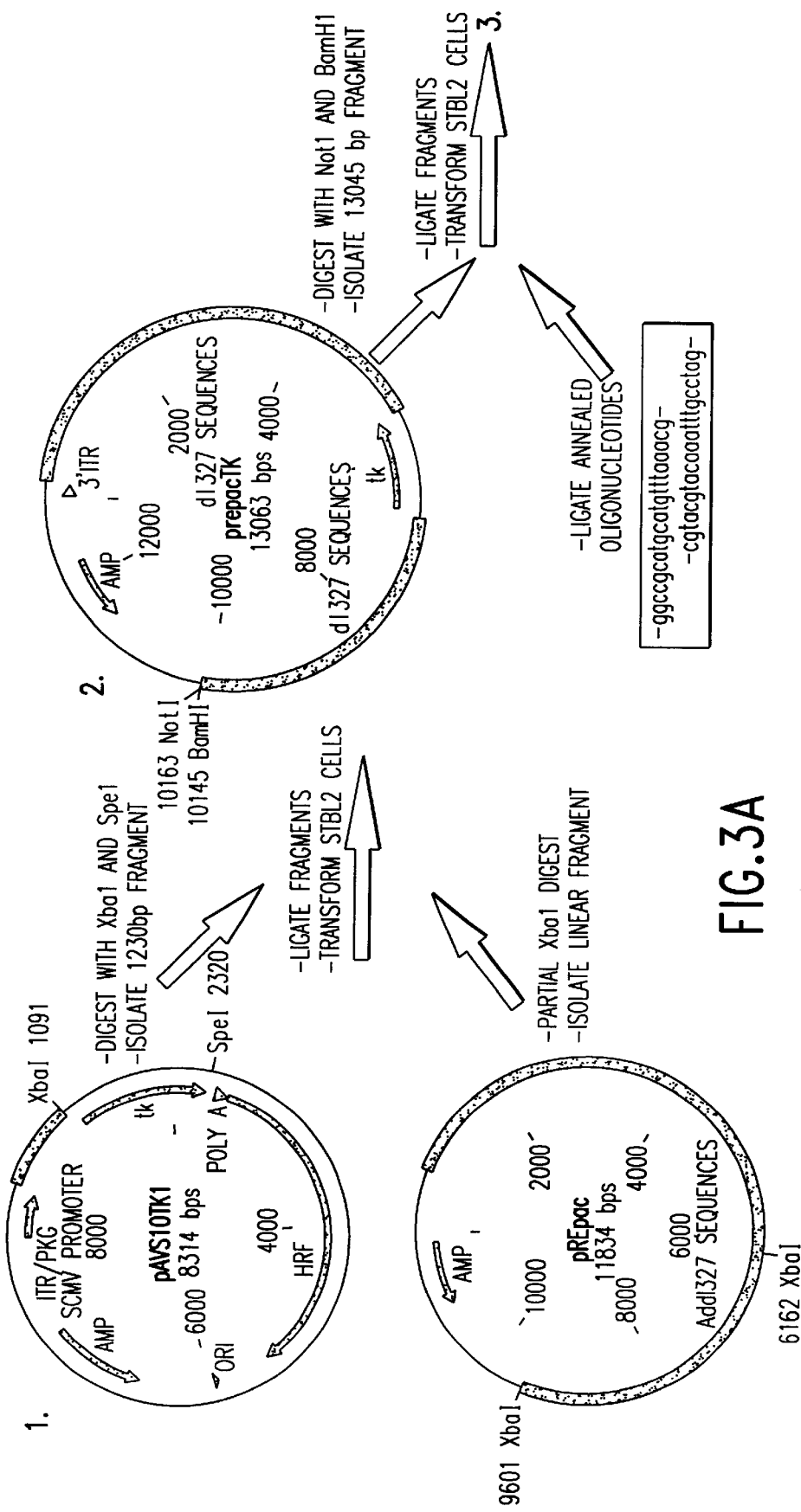
FIG. 3A. Cloning of the plasmid pREpacTK.
Figure 3B:
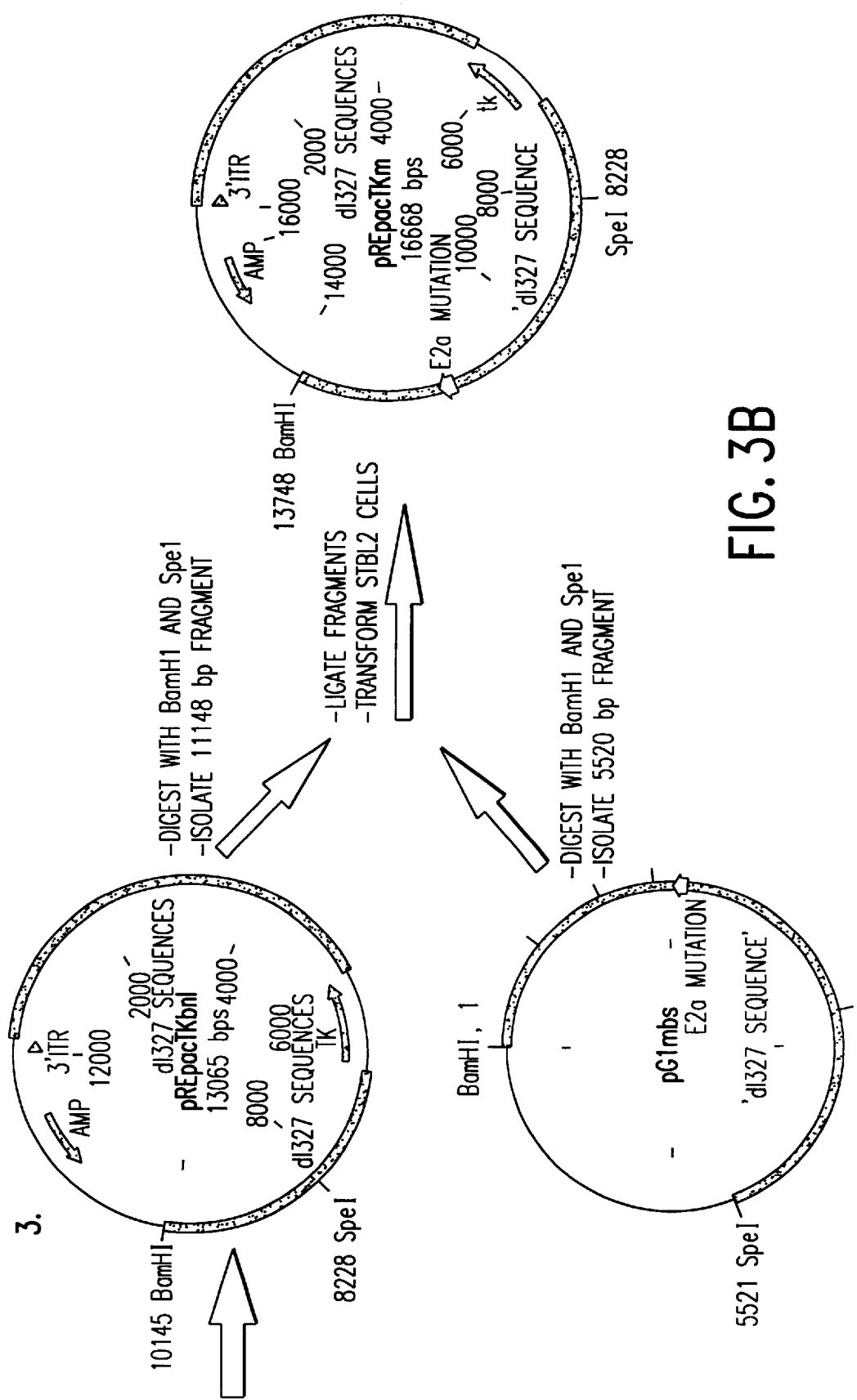
FIG. 3B. Cloning of the plasmid pREpacTKm.

AV5E1aTK01i Construction pAVS10TK1 (U.S. application Ser. No. 08/444,284) (the source of the TK gene in Av15EKa04i below) was digested with XbaI and SpeI and the resulting 1230 bp fragment, containing the HSV-TK open reading frame, was ligated into the partially digested XbaI site at base pair position 6162 of prepac (FIG. 3A) (described in U.S. patent application Ser. No. 08/852, 924). This shuttle plasmid contains the last 8886 base pairs from 25171 through 34057 of the Add1327 genome (Thimmapaya, Cell 31:543 (1983)) cloned into pBluescript SKII(+) (Stratagene). Prepac (FIG. 3A) is a large plasmid that contains the adenoviral genomic DNA from the right ITR through the E3 region. The TK gene derived from pAVS10TKI was inserted into the XbaI site in prepac, putting this gene under the control of the E3 promoter. The resulting ligated plasmid DNA was transformed into E. coli STBL2 cells (Life Technologies) and labeled as prepacTK. The plasmid prepacTK was then used to make the plasmid prepacTKbnl (FIG. 3B) by ligating the following two annealed oligonucleotides (5'-GGCCGCATGCATGTTTAAACG-3' (SEQ ID NO:1) and 5'-GATCCGTTTAAACATGCATGC-3') (SEQ ID NO:2) into the BamHI and NotI digested sites of prepacTK (FIGS. 3A, 3B). The ligation of this oligonucleotide creates another BamHI site without destroying the open reading frame.

The plasmid prepacTKm was then cloned by digesting prepacTKbnl with BamHI and SpeI and isolating the resulting 11148 base pair fragment (FIG. 3B). This removes a portion of the E2a gene and allows it to be replaced with a modified E2a gene containing a mutation that permits replication in monkey cells (from pG1MBS, see below). This 11198 base pair fragment was ligated to the 5520 base pair fragment obtained by digesting the plasmid pG1MBS with BamHI and SpeI (FIG. 3B). The final plasmid is designated prepacTKm. This plasmid has the TK gene in the E3 region, and also contains the E2a mutation as explained below.

The plasmid pG1MBS contains the adenoviral type 5 (Ad5) region between the BamHI site and the SpeI site (Ad5 genome base pair positions 21562 to 27082, respectively, FIG. 3B). Plasmid pG1MBS has a point mutation in the adenoviral sequences at base pair 11670 which allows for increased adenoviral replication in monkeys (as described by Kruijen, Nucl. Acids Res. 9:4439 (1981).

Figure 3C:
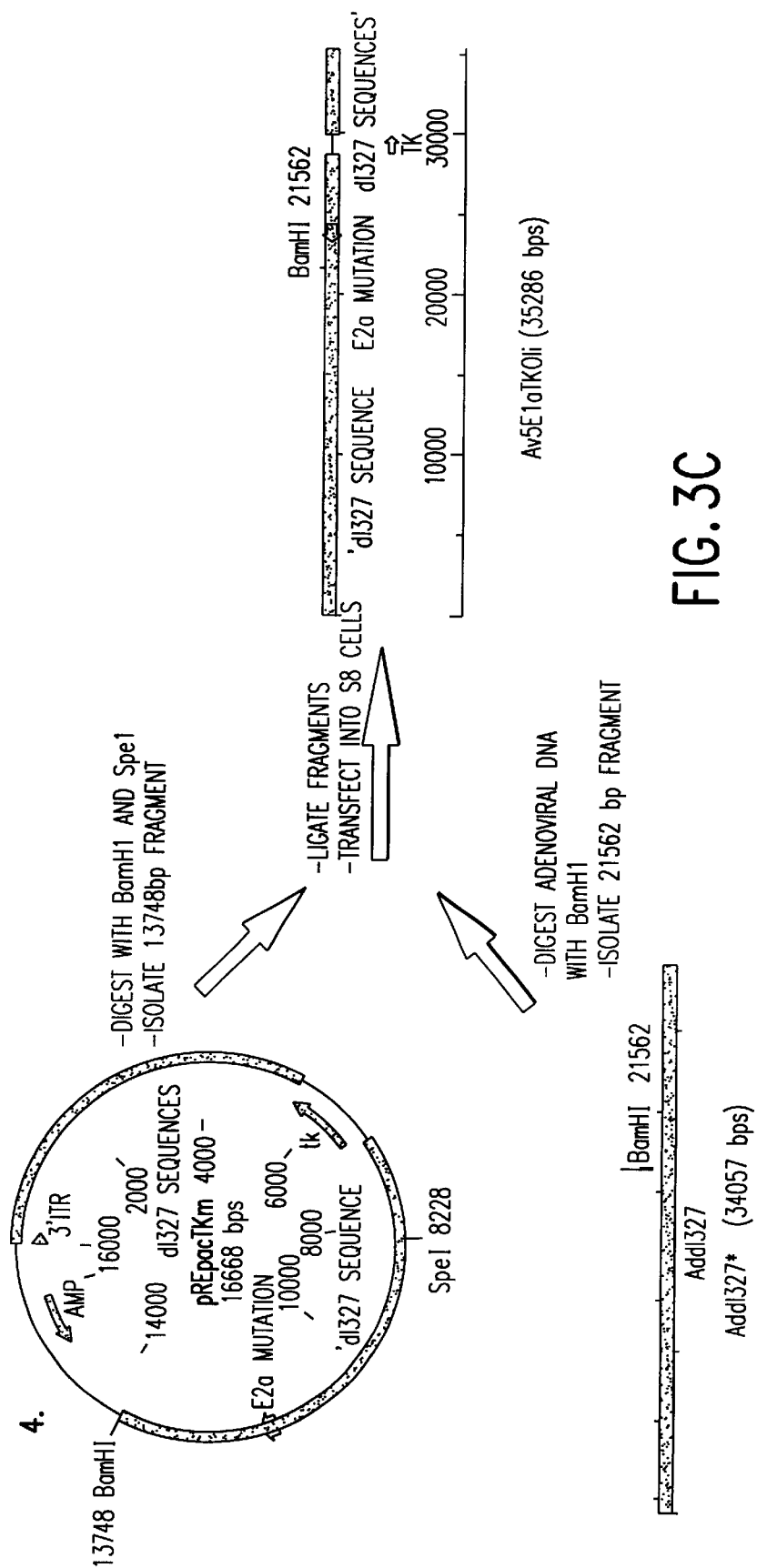
FIG. 3C. Construction of AV5E1aTK01i.

To prepare the adenoviral vector Av5E1aTK01i the plasmid pREpacTKm (FIG. 3C) was digested with the restriction enzymes BamHI and SalI and the 13748 base pair fragment was isolated by agarose gel electrophoresis. Adenovirus Add1327 DNA was prepared by digesting cesium density gradient centrifugation purified virus with Proteinase K. The Proteinase K digested Add1327 viral DNA was then extracted first with phenol/chloroform followed by chloloform and finally with buffer saturated ether. The DNA was recovered after equlibrating in water using an Amicon Centricon 100 unit. The purified Add1327 DNA was then digested with BamrHI and the 21562 base pair fragment was isolated by agarose gel electrophoresis. The 13748 base pair BamHI/SalI fragment from pREpacTKm and the 21562 base pair Bam HI fragment from Add1327 were then ligated together. The resulting ligated fragments were then transfected into A549.A30.S8 cells using Lipofectamine (Life Technologies Inc.) and incubated at 37° C. in a 5% $CO_2$, humidified, incubator until cytopathic effects (CPE) were observed. The resulting recombinant Av5E1aTK01i (FIG. 3C) virus was then plaque purified on A549.A30.S8 cells. Av5E1aTK01i plaques were screened by PCR for the presence of HSV-TK sequences using the following primers: (LMCI1: 5'-AGCAAGAAGCCACGG AAGTC-3' (SEQ ID NO:3) and LMC12: 5'-AGGTCGCAGATCGTCGGTAT-3') (SEQ ID NO:4).

Av15E1a04i Construction

Figure 4A:
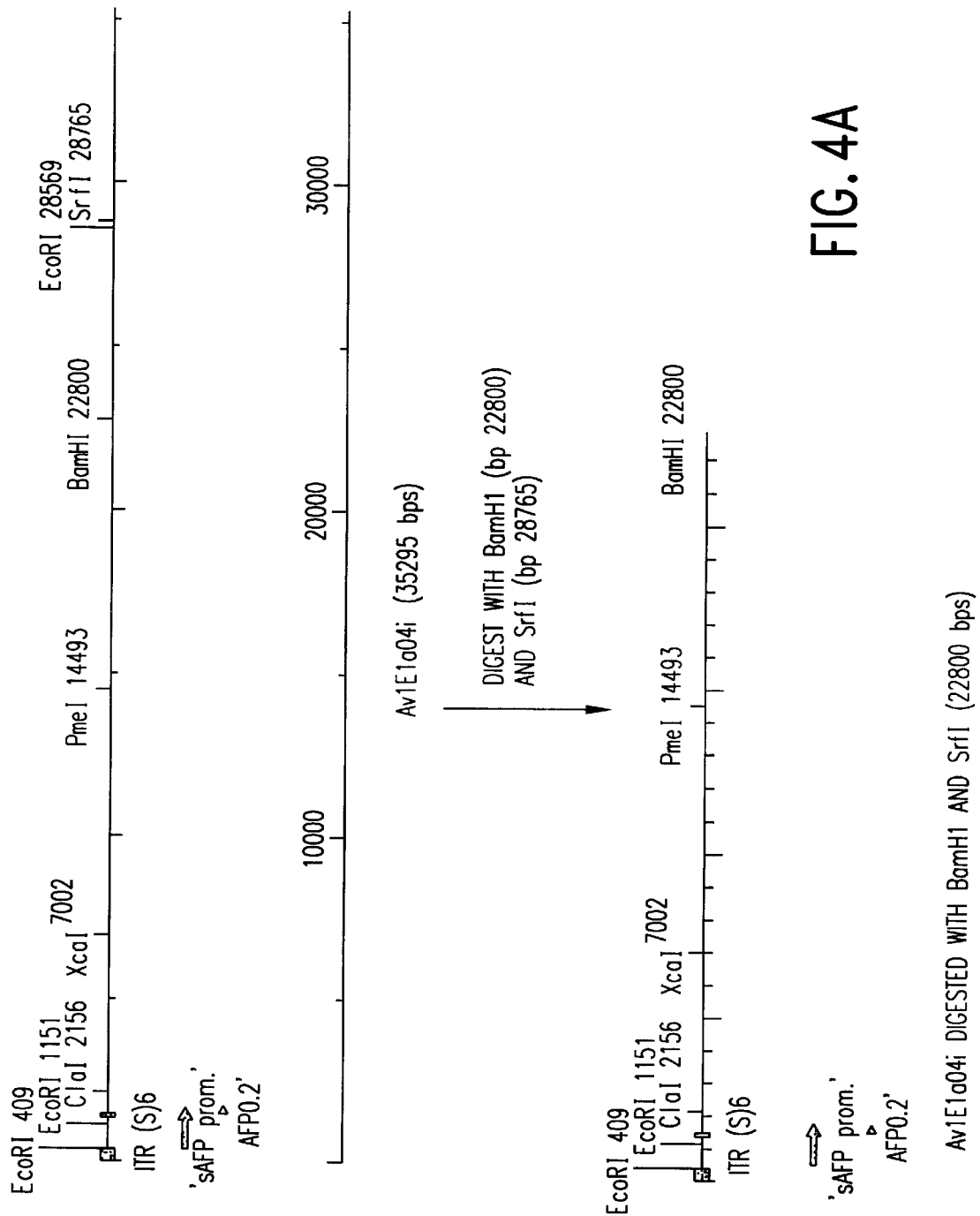
FIG. 4A. Digestion of Av1E1a04i.

Av1E1a04i was completely digested with SrfI (FIG. 4A) confirmed digestion on 1% agarose gel in 1×TAE, organic extracted digest with buffered phenol, buffered phenol/chloroform/isoamyl alcohol (25:24:1), and chloroform, and then added 1/10 volume 3M NaOAc and 2.5 volume 95% EtOH to precipitate. The precipitate was pelleted by 20 minute centrifugation at 12000 g, washed 1× with 70% EtOH, and then air dried for 30 minutes. The pellet was resuspended in $dH_2O$ and digested with BamHI. The complete digestion was confirmed and purified as before.

Figure 4B:
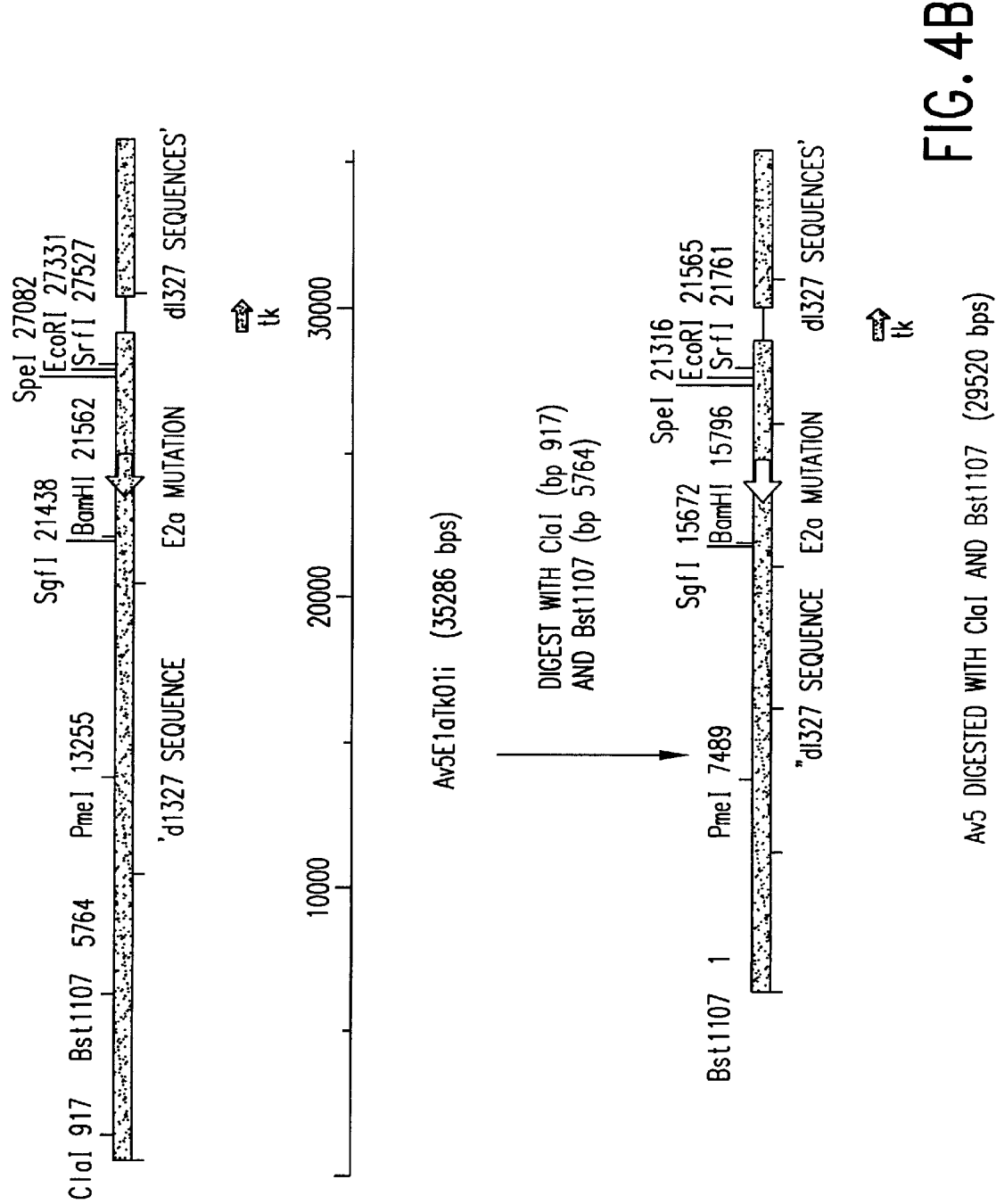
FIG. 4B. Digestion of Av5E1aTK01i.
Figure 4C:
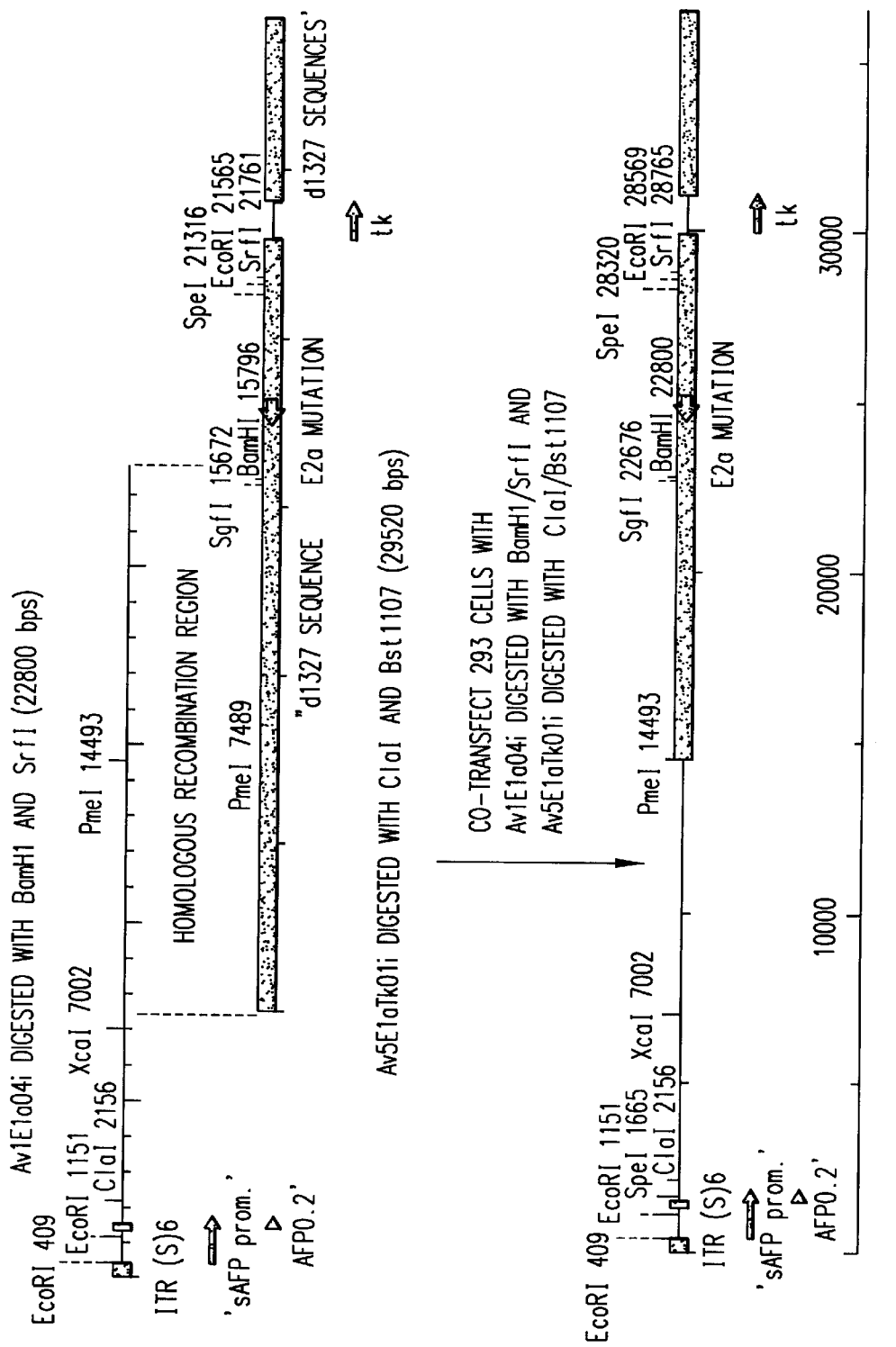
FIG. 4C. Construction of Av15E1aTK04i using the digestion products of FIGS. 4A and 4B.

293 cells were cotransfected with 2.5 ug Av5E1aTk01i (digested with Bst 1107 and ClaI (FIG. 4B) and 2.5 ug Av1E1a04i (digested with Bam HI and SrfI, FIG. 4A) using Promega $CaCl_2$ Transfection Kit (FIG. 4C). Transfections were washed 1× with Richters media supplemented with 10% FBS (R10) and then overlaid with 1×MEM/10% FBS/0.5% Pen-Strep/1% Fungizone. Plaques were identified by microscopic examination and picked with 1000 ul pipet tip into 500 ul R5 media. Plaques were lysed by freeze-thaw (4×) and then infected into S8 cells stimulated with 0.3 um dexamethasone. When early CPE was evident, the cells were washed 1× with PBS, lysed with 200 ul 1N NaOH and neutralized with 30 ul of 7.5 M ammonium acetate. The CVL was diluted 1:50 in $dH_2O$ and 5 ul of the diluted lysate was used in a 50 ul PCR reaction using the BMB master mix reagents.

E1a promoter primer pair detects both Av15E1aTk04i (1653 bp) and Add1327 (405 bp)

CH12 5'-GACCGTTTACGTGGAGACTCGC-3' (SEQ ID NO:5) bp 367 in ITR

CH13 5'-ACCGCCAACATTACAGAGTCG-3' (SEQ ID NO:6) bp 772 or bp 2020 in E1a gene of Add1327 or Av15E1aTk04i, respectively.

HSV-TK primer pair 990 bp product in either Av15E1aTk04i or Av5E1aTk01i

LMC11 5'-AGCAAGAAGCCACGGAAGTC-3' bp 100 of HSV-Tk ORF (SEQ ID NO:3)

LMC12 5'-AGGTCGCAGATCGTCGGTAT -3' bp 1090 of HSV-Tk ORF (SEQ ID NO:4)

Three primary plaques were identified for additional plaque purification on S8 cells using same PCR of CVL to identify positive plaques. One plaque was subsequently purified three times by plaque purification on S8 cells. A bulk preparation of the tertiary plaque for Av15E1aTk04i has a titer of $9 \times 10^{10}$ particles/ml, ratio 26.

Av15E1aTk04i (FIG. 4C) has the AFP promoter controlling E1a expression, and thus, only AFP positive cells are permissive for vector replication. Av15E1aTk04i also has an E2a mutation (hr404) which makes monkey cells permissive for replication, potentially expanding the range of permissive species to additional restricted species. Finally, Av15E1aTk04i has HSV-TK under the control of the E3 promoter which is positively regulated by E1a; therefore, there should be no expression in the absence of E1a, which will only be present in AFP positive cells. As a safety feature in the event that replication occurs in nontarget cells, then only the nontarget and target cells that are replicating vector would be sensitive to GCV treatment. Any infected, nontarget cells that are not replicating vector will be insensitive to GCV.

EXAMPLE 3

Figure 5:
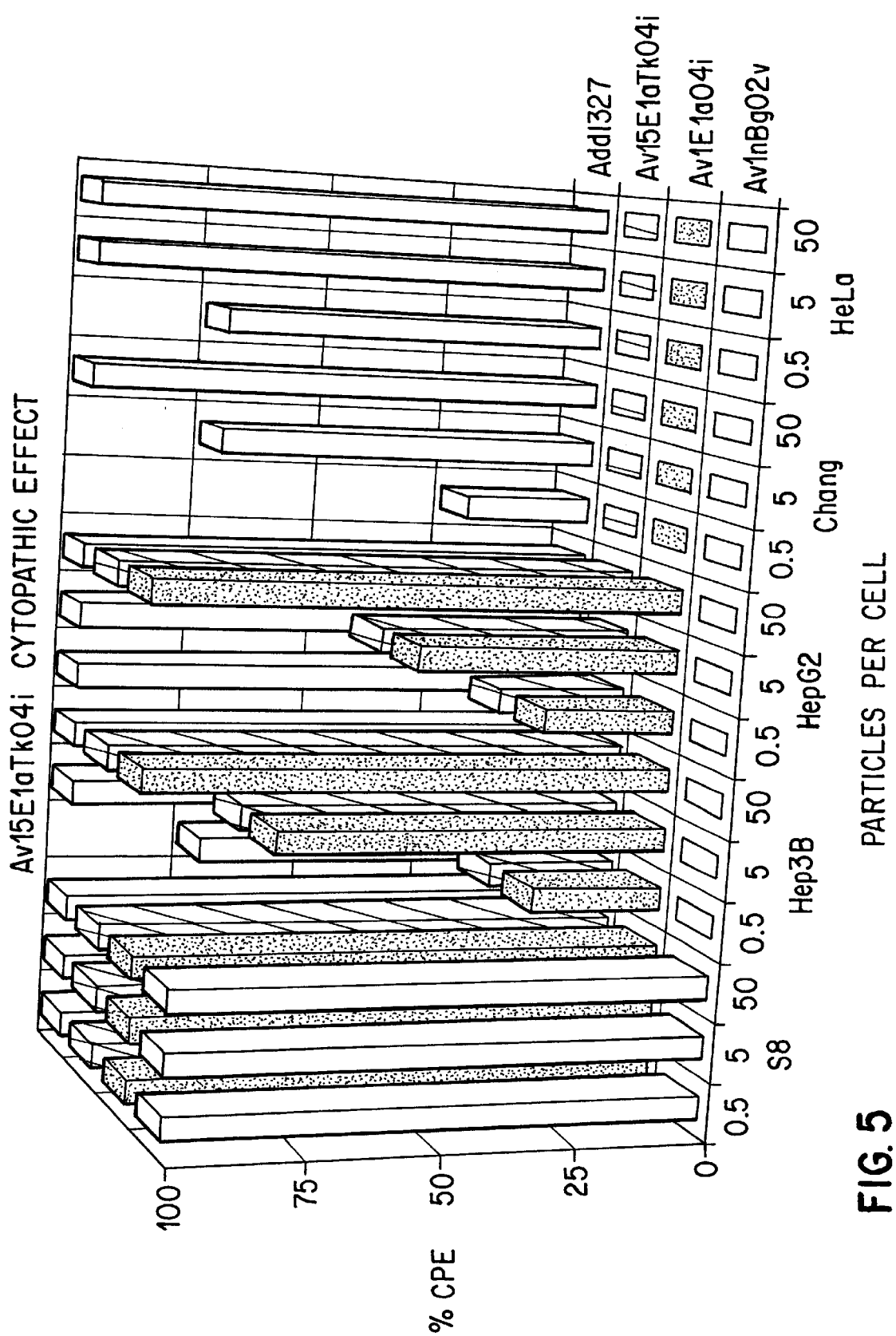
FIG. 5. Cytopathic effect of Av15E1aTK04i.

Av15E1aTk04i should have the same tissue specific replication restricted adenoviral profile as Av1E1a04i, specifically, replication only in AFP positive cells (as described in PCT Appl. No. US 95/15455 (U.S. Pat. No. 5,998,205)). Infection of Hep3B and HepG2 (AFP positive hepatocellular carcinoma cell lines) and S8 (E1a positive cell line) with Add1327, Av1E1a04i, or Av15E1aTk04i results in visible CPE at infections of 0.5, 5, and 50 particle per cell (FIG. 5). Av1nBg02v (E1 deleted virus) infection at the same input particle numbers exhibit no visible CPE except in S8 cells. Conversely, Chang and HeLa (AFP negative cell lines) exhibit visible CPE only when infected with Add1327 (wild type) when infected at the same input particles. Av1E1a04i, Av15E1aTk04i, and Av1nBg02v all manifest no CPE at infections of 0.5, 5, and 50 particle per cell in Chang and HeLa cells (FIG. 5). This indicates that AV15E1aTK04i also replicates specifically in AFP-positive cell lines. Therefore, the E1a gene product, which controls the E3 promoter, must also be induced specifically in AFP-positive cell lines. Therefore, HSV-TK, which is controlled by the E3 promoter, is also induced specifically in AFP-positive cell lines.

EXAMPLE 4

Replacement of Other Therapeutic Toxic Genes Into the Tumor-specific Replication Competent Vectors Genes such as TK, cytokines, or any therapeutic genes can be placed into to the E3 region of the vector backbone by standard plasmid construction and homologous recombination. Those genes can be placed under the control of an E1a-dependent promoter, or a constitutive promoter such as RSV or CMV.

Figure 6:
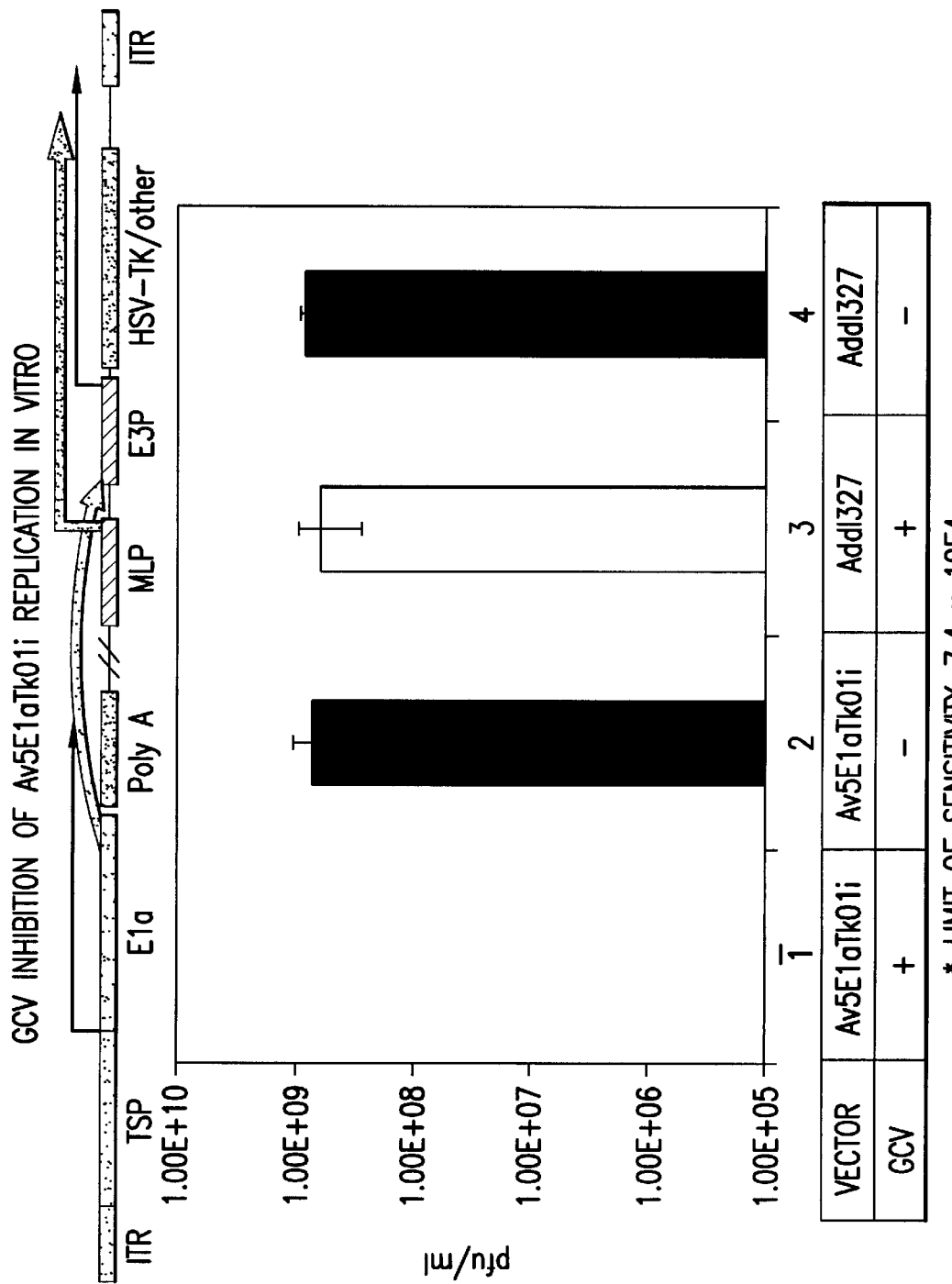
FIG. 6. GCV Inhibition of Av5E1aTk01i Replication In Vitro. A549 cells were transduced with either Add1327 or Add1327Tk01i. Cells were then treated with 10 uM GCV for 5 days. Following the 5 day incubation, cells were harvested, washed in HBSS, and then freeze/thawed to prepare a crude viral lysate. Titers were then performed by standard TCID50 assays on 293 cells to determine viral titer. The experiment was repeated three times. Results show that while GCV had no effect on an adenovirus not carrying the HSV-TK gene, it caused a greater than 4 order of magnitude drop in titer of a vector carrying the HSV-TK gene.

In vitro control of replication by inclusion of HSV-TK into the E3 region (FIG. 6).

HSV-TK was placed into the E3 region of Add1327 to form Av5E1aTK01i. A549 cells were transduced with either Add1327 or Av5E1aTK01i. Cells were then treated with 10 $\mu$M GCV for 5 days. Following the 5 day incubation cells were harvested, washed in HBSS, and then freeze/thawed to prepare a crude viral lysate. Titers were then performed by standard TCID$^{50}$ assays on 293 cells to determine viral titer. The experiment was repeated three times. Results show that while GCV had no effect on an adenovirus not carrying the HSV-TK gene, it caused a greater than 4 order of magnitude drop in titer of a vector carrying the HSV-TK gene.

In vivo control of replication by inclusion of HSV-TK into E3 region (FIG. 7).

Subcutaneous tumors were formed by injecting 1×10$^7$ A549 cells into the subcutaneous space of the right flank of nude mice. After tumors formed, 1×10$^9$ pfu of Av5E1aTK01i was injected into several animals containing tumors. After 5 days half the animals received 5 days of IP GCV treatment at 75 mg/kg once a day. At the end of this time frame all animals were sacrificed. Immunohistochemistry was performed on all samples for HSV-TK expression and hexon expression, the latter which is only expressed when the vector is replicating. Results show as seen in the figure that only hexon is severely diminished when the animals were treated with GCV.

The disclosures of all patents, publications (including published patent applications), and database accession numbers referred to in this specification are specifically incorporated herein by reference in their entirety to the same extent as if each such individual-patent, publication, and database accession numbers were specifically and individually indicated to be incorporated by reference in its entirety.

TABLE 1

Oligonucleotide Primers for Constructing Tissue-Specific Promoters

1. DF3 (Breast Cancer)

```
                                         (SEQ ID NO:7)
5' GGG CGC GCC CTG GAA AGT CCG GCT GGG GCG
   GGG ACT GTG GGT TTC AGG GTA GAA CTG CGT
   GTG GAA           3'
                                         (SEQ ID NO:8)
5' CGG GAC AGG GAG CGG TTA GAA GGG TGG GGC
   TAT TCC GGG AAG TGG TGG GGG GAG GGA ACT
   AGT A             3'
                                         (SEQ ID NO:9)
5' GAT CTA CTA GTT CCC TCC CCC CAC CAC TTC
   CCG GAA TAG CCC CAC CCT TCT AAC CGC TCC
   CTG               3'
                                        (SEQ ID NO:10)
5' TCC CGT TCC ACA CGC AGT TCT ACC CTG AAA
   CCC ACA GTC CCC GCC CCA GCC GGA CTT TCC
   AGG GCG CGC CC    3'
```

2. Tyrosinase (Melanoma)

```
                                        (SEQ ID NO:11)
5' GAC CCG GGC GCG CCG GAG CAG TGC TAT TCA
   AAC CAT CCA G     3'
                                        (SEQ ID NO:12)
5' CGA GAT CTA CTA GTT CTG CAC CAA TAG GTT
   AAT GAG TGT C     3'
```

3. CEA Promoter (Hepatocellular Carcinoma)

```
                                        (SEQ ID NO:13)
5' GAC CCG GGC GCG CCT CTG TCA CCT TCC TGT
   TTG               3'
                                        (SEQ ID NO:14)
5' CGA GAT CTA CTA GTT CTC TGC TGT CTG CTC
   TGT C             3'
```

What is claimed is:

1. A tissue-specific replication-conditional adenoviral vector comprising:

(a) a heterologous tissue-specific transcriptional regulatory sequence operably linked to the coding region of a gene that is essential for replication of said vector, wherein said coding region is an E1a, E1b, E2, or E4 coding region; and (b) at least one additional coding sequence encoding a heterologous gene product, wherein said additional coding sequence is operably linked to said heterologous tissue-specific transcrptional regulatory sequence.

2. The vector of claim 1, wherein said tissue-specific transcriptional regulatory sequence is a promoter or an enhancer.

3. The vector of claim 2, where said promoter is selected from the group consisting of an MUC1/DF3 promoter, an alpha-fetoprotein promoter, an erb-B2 promoter, a surfactant promoter, a thymidine kinase promoter, a p21 promoter, and a cyclin promoter.

4. The vector of claim 2, wherein said enhancer is selected from the group consisting of DF3, a breast cancer-specific enhancer, viral enhancers, and steroid receptor enhancers.

5. The vector of claim 1, wherein said additional coding sequence is selected from the group consisting of a thymidine kinase coding sequence, a cytosine deaminase coding sequence, and a purine nucleoside phosphorylase coding sequence.

6. An isolated cell comprising the vector of claim 1.

7. The cell of claim 6, wherein said vector replicates in said cell by means of said tissue-specific regulatory sequence, and in which cell said additional coding sequence is expressed.

8. The cell of claim 6, wherein said cell is a tumor cell or an abnormally proliferating cell.

9. The cell of claim 8, wherein said additional coding sequence provides a gene product that provides anti-tumor activity in said cell.

10. The cell of claim 8, wherein said tumor cell is selected from the group consisting of a hepatoma cell, and lung carcinoma cell.

11. A method of producing the vector of claim 1, comprising culturing a cell comprising said vector and recovering said vector from said cell.

12. The vector of claim 1, wherein said additional coding sequence expresses a gene product that can reduce or eliminate vector replication.

13. The vector of claim 12, wherein said gene product is selected from the group consisting of cytosine deaminase, thymidine kinase, and purine nucleoside phosphorylase.

14. A tissue-specific replication-conditional adenoviral vector comprising:
    (a) a heterologous tissue-specific transcriptional regulatory sequence operably linked to the coding region of the adenovirus E1a gene that is essential for replication of said vector; and
    (b) at least one additional coding sequence encoding a heterologous gene product, wherein said additional coding sequence is operably linked to a second transcriptional regulatory sequence that is activated by the E1a gene product.

15. The vector of claim 14, wherein said at least one additional coding sequence replaces a coding sequence of a gene in said vector, which gene is not essential for vector replication, such that said at least one additional coding sequence is operably linked to and transcribed from said second transcriptional regulatory sequence.

16. The vector of claim 10, wherein at least one of said transcriptional regulatory sequences is a promoter or an enhancer.

17. The vector of claim 16, where said promoter is selected from the group consisting of an MUC1/DF3 promoter, an alpha-fetoprotein promoter, an erb-B2 promoter, a surfactant promoter, a thymidine kinase promoter, a p21 promoter, and a cyclin promoter.

18. The vector of claim 16, wherein said enhancer is selected from the group consisting of DF3, a breast cancer-specific enhancer, a viral enhancer, and a steroid receptor enhancer.

19. The vector of claim 14, wherein said additional coding sequence is selected from the group consisting of a thymidine kinase coding sequence, a cytosine deaminase coding sequence, and a purine nucleoside phosphorylase coding sequence.

20. The vector of claim 14, wherein said at least one additional coding sequence encodes a gene product that can reduce or eliminate replication of said vector.

21. The vector of claim 20, wherein said gene product is selected from the group consisting of cytosine deaminase, thymidine kinase, and purine nucleoside phosphorylase.

22. An isolated cell comprising the vector of claim 14.

23. The cell of claim 22, wherein said vector replicates in said cell by means of said tissue-specific regulatory sequence operably linked to the coding region of the adenovirus E1a gene, and in which cell said at least one additional coding sequence is expressed.

24. The cell of claim 22, wherein said cell is a tumor cell or an abnormally proliferating cell.

25. The cell of claim 24, wherein said at least one additional coding sequence encodes a gene product that provides anti-tumor activity in said cell.

26. The cell of claim 24, wherein said tumor cell is selected from the group consisting of a hepatoma cell and lung carcinoma cell.

27. A method of producing the vector of claim 14, comprising culturing a cell comprising said vector and recovering said vector from said cell.

28. The vector of claim 1, wherein said transcriptional regulatory sequence is a tumor-specific regulatory sequence.

29. The vector of claim 28, wherein said tumor-specific regulatory sequence is a tumor-specific promoter.

30. The vector of claim 1, wherein said transcriptional regulatory sequence is an alpha-fetoprotein promoter.

31. The vector of claim 1, wherein said coding region is the E1a coding region.

32. The vector of claim 1, wherein said coding region is the E1b coding region.

33. The vector of claim 1, wherein said coding region is the coding region.

34. The vector of claim 33, wherein said coding region is the coding region.

35. The vector of claim 1, wherein said coding region is the E4 coding region.

36. The vector of claim 1, wherein said additional coding sequence is a thymidine kinase coding sequence.

37. The cell of claim 6, wherein said transcriptional regulatory sequence is a tumor-specific regulatory sequence.

38. The vector of claim 37, wherein said tumor-specific regulatory sequence is a tumor-specific promoter.

39. The cell of claim 6, wherein said transcriptional regulatory sequence is an alpha-fetoprotein promoter.

40. The cell of claim 6, wherein said coding region is the E1a coding region.

41. The cell of claim 6, wherein said coding region is the E1b coding region.

42. The cell of claim 6, wherein said coding region is the coding region.

43. The cell of claim 42, wherein said coding region is the coding region.

44. The cell of claim 6, wherein said coding region is the E4 coding region.

45. The cell of claim 6, wherein said additional coding sequence is a thymidine kinase coding sequence.

46. The vector of claim 14, wherein said transcriptional regulatory sequence operably linked to the coding region of the adenovirus E1a gene is a tumor-specific regulatory sequence.

47. The vector of claim 46, wherein said tumor-specific regulatory sequence operably linked to the coding region of the adenovirus E1a gene is a tumor-specific promoter.

48. The vector of claim 14, wherein said transcriptional regulatory sequence operably linked to the coding region of the adenovirus E1a gene is an alpha-fetoprotein promoter.

49. The vector of claim 14, wherein said at least one additional coding sequence replaces a coding sequence of the adenovirus E3 gene in said vector, such that said at least one additional coding sequence is operably linked to and transcribed from said second transcriptional regulatory sequence.

50. The vector of claim 49, wherein said second transcriptional regulatory sequence is an adenovirus E3 promoter.

51. The vector of claim 14, wherein said additional coding sequence is a thymidine kinase coding sequence.

52. The vector of claim 50, wherein said additional coding sequence is a thymidine kinase coding sequence.

53. The cell of claim 22, wherein said transcriptional regulatory sequence operably linked to the coding region of the adenovirus E1a gene is a tumor-specific regulatory sequence.

54. The cell of claim 53, wherein said tumor-specific regulatory sequence operably linked to the coding region of the adenovirus E1a gene is a tumor-specific promoter.

55. The cell of claim 22, wherein said transcriptional regulatory sequence operably linked to the coding region of the adenovirus E1a gene is an alpha-fetoprotein promoter.

56. The cell of claim 22, wherein said at least one additional coding sequence replaces a coding sequence of the adenovirus E3 gene in said vector, such that said at least one additional coding sequence is operably linked to and transcribed from said second transcriptional regulatory sequence.

57. The cell of claim 56, wherein said second transcriptional regulatory sequence is an adenovirus E3 promoter.

58. The cell of claim 22, wherein said additional coding sequence is a thymidine kinase coding sequence.

59. The cell of claim 57, wherein said additional coding sequence is a thymidine kinase coding sequence.

* * * * *

UNITED STATES PATENT AND TRADEMARK OFFICE
CERTIFICATE OF CORRECTION

PATENT NO. : 6,638,762 B1
DATED : October 28, 2003
INVENTOR(S) : Yung-Nien Chang et al.

It is certified that error appears in the above-identified patent and that said Letters Patent is hereby corrected as shown below:

Title page, Item [54] and Column 1, lines 1-2,
Title, should read as follows: -- VECTOR FOR TISSUE-SPECIFIC REPLICATION AND GENE EXPRESSION --

Column 42,
Lines 38-41 and 56-59, please replace claims 33, 34, 42 and 43 with the following:

-- 33. The vector of claim 1, wherein said coding region is the E2 coding region.
34. The vector of claim 33, wherein said coding region is the E4 coding region.
42. The vector of claim 6, wherein said coding region is the E2 coding region.
43. The vector of claim 42, wherein said coding region is the E4 coding region. --

Signed and Sealed this

Nineteenth Day of October, 2004

JON W. DUDAS
*Director of the United States Patent and Trademark Office*